United States Patent [19]
Bandman et al.

[11] Patent Number: 6,043,343
[45] Date of Patent: Mar. 28, 2000

[54] TUMOR PROTEINS

[75] Inventors: Olga Bandman, Mountain View; Janice Au-Young, Berkeley; Surya K. Goli, Sunnyvale; Jennifer L. Hillman, San Jose, all of Calif.

[73] Assignee: Incyte Pharmaceuticals, Inc., Palo Alto, Calif.

[21] Appl. No.: 09/162,597

[22] Filed: Sep. 29, 1998

Related U.S. Application Data

[62] Division of application No. 08/715,204, Sep. 17, 1996, Pat. No. 5,874,286.

[51] Int. Cl.$^7$ .......................... C07K 14/47; C07K 16/18; C07K 16/30; A61K 38/17; G01N 33/53
[52] U.S. Cl. .................. 530/350; 530/300; 530/387.1; 530/387.7; 530/388.8; 530/389.7; 435/7.1; 435/7.21; 435/7.23; 514/2
[58] Field of Search ..................... 530/300, 350, 530/387.1, 387.7, 388.8, 389.7; 514/2; 435/7.1, 7.21, 7.23

[56] References Cited

FOREIGN PATENT DOCUMENTS 97 06256   2/1997   WIPO .

OTHER PUBLICATIONS

A. Lehninger "Biochemistry" New York: Worth Publishers, p. 962 1975.

Bryne, J.A., et al., "A Screening Method to Identify Genes Commonly Overexpressed in Carcinomas and the Identification of a Novel Complementary DNA Sequence", *Cancer Res.*, 55:2896–2903 (1995).

Bryne J.A., et al., "Definition of the Tumor Protein D52 (TPD52) Gene Family through Cloning of D52 Homologues in Human (hD53) and Mouse (mD52)", *Genomics*, 35:523–532 (1996).

Chen, S.L., et al., "Isolation and characterization of a novel gene expressed in multiple cancers", *Oncogene*, 12:741–751 (1996).

Kern, J.A., et al., "Inhibition of Human Lung Cancer Cell Line Growth by an Anti–p185$^{HER2}$ Antibody", *Am J Respir Cell Mol Biol*, 9:448–454 (1993).

Liu, E. et al., "The HER2 (c–erbB–2) oncogene is frequently amplified in in situ carcinomas of the breast", *Oncogene*, 7:1027–1032 (1992).

Loetscher, P. et al., "The C Terminus of Mouse Ornithine Decarboxylase Confers Rapid Degradation on Dihydrofolate Reductase", *J Biol Chem*, 266:11213–11220 (1991).

Rechsteiner, M., "PEST sequences are signals for rapid intracellular proteolysis", *Cell Biol*, 1:433–440 (1990).

Wilson, R. et al., "2.2 Mb of contiguous nucleotide sequence from chromosome III of C. Elegans", *Nature*, 368:32–38 (1994).

*Primary Examiner*—Nancy A. Johnson
*Attorney, Agent, or Firm*—Danielle Pasqualone; Incyte Pharmaceuticals, Inc.

[57] ABSTRACT

The present invention provides novel human tumor proteins (collectively called TUPRO) and polynucleotides which identify and encode TUPRO. The invention also provides genetically engineered expression vectors and host cells comprising the nucleic acid sequences encoding TUPRO. The invention also provides pharmaceutical compositions containing TUPRO or antagonists to TUPRO, and in the use of these compositions for the treatment of diseases associated with the expression of TUPRO. Additionally, the invention provides for the use of antisense molecules to polynucleotides encoding TUPRO for the treatment of diseases associated with the expression of TUPRO. The invention also provides diagnostic assays which utilize the polynucleotide, or fragments or the complement thereof, to hybridize to the genomic sequence or transcripts of polynucleotides encoding TUPRO or anti-TUPRO antibodies which specifically bind to TUPRO.

4 Claims, 15 Drawing Sheets

```
                                                9                18            27           36            45            54
          5' GCC AGC TGC GTT CTG AGC CTG GGC GCA GCT ACC ATC TGC TCT GGG AAG CAC CAG 63            72            81            90            99           108
             GGT GTC CCC GCC GCC CTC AGC TCG AAG TCA GCC ACC ATG GAG GCG CAG GCA CAA
                                                                    M   E   A   Q   A   Q 117           126           135           144           153           162
             GGT TTG GAG ACT GAA CCG TTG CAA GGA ACA GAC GAA GAT GCA GTA GCC AGT
              G   L   E   T   E   P   L   Q   G   T   D   E   D   A   V   A   S 171           180           189           198           207           216
             GCT GAC TTC TCT AGC ATG CTC TCT GAG GAG AAG GAA GAG TTA AAA GCA GAG
              A   D   F   S   S   M   L   S   E   E   K   E   E   L   K   A   E 225           234           243           252           261           270
             TTA GTT CAG CTA GAA GAC GAA ATT ACA ACA CTA CGA CAA GTT TTG TCA GCG AAA
              L   V   Q   L   E   D   E   I   T   T   L   R   Q   V   L   S   A   K 279           288           297           306           315           324
             GAA AGG CAT CTA GTT GAG ATA AAA CAA AAA CTC GGC ATG AAC CTG ATG AAT GAA
              E   R   H   L   V   E   I   K   Q   K   L   G   M   N   L   M   N   E 333           342           351           360           369           378
             TTA AAA CAG AAC TTC AGC AAA AGC TGG CAT GAC ATG CAG ACT ACC ACT GCC TAC
              L   K   Q   N   F   S   K   S   W   H   D   M   Q   T   T   T   A   Y
```

FIGURE 1A

```
      387         396         405         414         423         432
AAG AAA ACA CAT GAA ACC CTG AGT CAC GCA GGG CAA AAG CAC ACT GCA GCT TTC
 K   K   T   H   E   T   L   S   H   A   G   Q   K   H   T   A   A   F 441         450         459         468         477         486
AGC AAC GTT GGA ACG ATG ATG CCT GCC ATC AGC AAG AAG TTC GGA GAC ATG AGT TAC TCC ATT
 S   N   V   G   T   M   M   P   A   I   S   K   K   F   G   D   M   S   Y   S   I 495         504         513         522         531         540
CGC CAT TCC ATA AGT ATG CCT GCT ATG AGG AAT TCT CCT ACT TTC AAA TCA TTT
 R   H   S   I   S   M   P   A   M   R   N   S   P   T   F   K   S   F 549         558         567         576         585         594
GAG AGG GTT GAG ACA ACT GTC ACA AGC CTC AAG ACG AAA TTC GTA GGC GGT ACG
 E   R   V   E   T   T   V   T   S   L   K   T   K   F   V   G   G   T 603         612         621         630         639         648
AAC CCT AAT GGA GGC AGT TTT GAG GAG GTC CTC AGC TCC ACG AGC GCC CAT GCC AGT
 N   P   N   G   G   S   F   E   E   V   L   S   S   T   S   A   H   A   S 657         666         675         684         693         702
GCC CAG AGC TTG GCA GGA GGC TCC CGG CGG ACC AAG GAG GAG GAG CTG CAG TGC
 A   Q   S   L   A   G   G   S   R   R   T   K   E   E   E   L   Q   C 711         720         729         738         747         756
TAA GTC CAG CCA GCG TGC AGT GCA TCC AGA AAC CGG CCA CTA CCC AGC CCA TCT
```

FIGURE 1B 765   774   783
NTG CCT GTG CTT ATC CAG ATA AGA AGA CCA AA 3'

FIGURE 1C

```
                                                9              18          27          36          45           54
5' TMG MKC GCG GGC CCC CGC CAG TCA GGT GGG TGC CAG GCC CTG GCC GTG GCG AAA 63          72          81          90          99          108
GAG CCG GCG GAG GGA CCC GCT CCC GGA GAC GCC GCC TCG CGA TCC CCG CGC 117         126         135         144         153         162
GGG CGG GAC CGG GCG GGC ATC ATG ACC CTG TTT CAC TTT GGG AAC TGC TTC
                             M   T   L   F   H   F   G   N   C   F 171         180         189         198         207         216
GCT CTT GCC TTC CCC TAC TTC ATC ACC TAC AAG TGC AGC GGC CTG TCC GAG
 A   L   A   F   P   Y   F   I   T   Y   K   C   S   G   L   S   E 225         234         243         252         261         270
TAC AAC GCC TTC TGG AAA TGC GTC CAG GCT GGA GTC ACC TAC CTC TTT GTC CAA
 Y   N   A   F   W   K   C   V   Q   A   G   V   T   Y   L   F   V   Q 279         288         297         306         315         324
CTC TGC AAG ATG CTG TTC TTG GCC ACT TTC TTT CCC ACC TGG GAA GGC GGC ATC
 L   C   K   M   L   F   L   A   T   F   F   P   T   W   E   G   G   I 333         342         351         360         369         378
TAT GAC TTC ATT GGG GAG TTC ATG AAG GCC AGC GTG GAT GTG GCA GAC CTG ATA
 Y   D   F   I   G   E   F   M   K   A   S   V   D   V   A   D   L   I
```

FIGURE 2A

```
      387         396         405         414         423         432
GGT CTA AAC CTT GTC ATG TCC CGG AAT GCC GGC AAG GGA GAG TAC AAG ATC ATG
 G   L   N   L   V   M   S   R   N   A   G   K   G   E   Y   K   I   M 441         450         459         468         477         486
GTT GCT GCC CTG GGA GCC TGG GCC ACT GCT GAG CTT ATT ATG TCC CGC TGC ATT CCC
 V   A   A   L   G   A   W   A   T   A   E   L   I   M   S   R   C   I   P 495         504         513         522         531         540
CTA TGG GTC GGA GCC CGG GGC ATT GAG TTT GAC TGG AAG TAC ATC CAG ATG AGC
 L   W   V   G   A   R   G   I   E   F   D   W   K   Y   I   Q   M   S 549         558         567         576         585         594
ATA GAC TCC AAC ATC AGT CTG GTC CAT TAC ATC GTC GCG TCT GCT CAG GTC TGG
 I   D   S   N   I   S   L   V   H   Y   I   V   A   S   A   Q   V   W 603         612         621         630         639         648
ATG ATA ACA CGC TAT GAT CTG TAC CAC AAC TTC CGG CCA GCT GTC CTT CTG CTG
 M   I   T   R   Y   D   L   Y   H   N   F   R   P   A   V   L   L   L 657         666         675         684         693         702
ATG TTC CTC AGT GTC TAC AAG GCC TTT GTT ATG GAG ACC TTC GTC CAC CTC TGC
 M   F   L   S   V   Y   K   A   F   V   M   E   T   F   V   H   L   C 711         720         729         738         747         756
TCG CTG GGC AGT TGG GCA RCT CTA MTG GCC CGA GCA GTG GTA ACG GGG CTG CTG
 S   L   G   S   W   A   X   L   X   A   R   A   V   V   T   G   L   L
```

FIGURE 2B

```
         765              774              783              792              801              810
    GCC CTC AAG CAC TTT GGS CCT GTA TGT CGS CGT TGT CAA TGT GCA CTY CTA GGC
     A   L   K   H   F   G   P   V   C   R   R   C   Q   C   A   L   L   G 819              828              837              846              855              864
    TTG GTG TCT CAG ACA TTG ATG TAC CTT TTC CCT GCC TCA CTC CAG GTT TTA GTG
     L   V   S   Q   T   L   M   Y   L   F   P   A   S   L   Q   V   L   V 873              882
    AAG TAA ACA GTA TTT GGA AAG TT 3'
     K
```

FIGURE 2C

| Library | Lib Description | Abun | Pct Abun |
|---|---|---|---|
| BRAINOM02 | brain, 55 M, NORM, WM | 1 | 0.0454 |
| UTRSNOT01 | uterus, 59 F | 1 | 0.0393 |
| TLYMNOR01 | lymphocytes (non-adher PBMNC), 24 M, RP | 1 | 0.0372 |
| BRSTNOT02 | breast, 55 F, match to BRSTTUT01 | 2 | 0.0317 |
| PROSTUT08 | prostate tumor, 60 M, match to PROSNOT14 | 1 | 0.0266 |
| PROSNOT14 | prostate, 60 M, match to PROSTUT08 | 1 | 0.0256 |
| LIVRNOM01 | liver, 49 M, WM | 1 | 0.0254 |
| PROSTUT15 | prostate, 66 M, match to PROSTUT10 | 1 | 0.0241 |
| NERVMSM01 | multiple sclerosis, 46 M, NORM, WM | 1 | 0.0228 |
| HNT2AGT01 | hNT2 cell line, post-mitotic neurons | 1 | 0.0190 |
| BRAITUT02 | brain tumor, metastasis, 58 M | 1 | 0.0169 |
| LIVSFEM02 | liver/spleen, fetal M, NORM, WM | 2 | 0.0053 |

Electronic Northern Results returned a total of 12 row(s).

FIGURE 3

| Library | Lib Description | Abun | Pct Abun |
|---|---|---|---|
| COLNNOT22 | colon, 56 F | 2 | 0.0554 |
| COLNPOT01 | colon polyp, 40 F | 2 | 0.0513 |
| PROSNOT18 | prostate, hyperplasia, 58 M | 2 | 0.0513 |
| MUSCNOT02 | muscle, psoas, 12 M | 1 | 0.0382 |
| STOMTUT01 | stomach tumor, 52 M, match to STOMNOT02 | 1 | 0.0368 |
| SINTNOT02 | small intestine, 55 F | 1 | 0.0337 |
| LVENNOT03 | heart, left ventricle, 31 M | 1 | 0.0337 |
| MMLR3DT01 | macrophages (adher PBMNC), M/F, 72-hr MLR | 1 | 0.0331 |
| PROSTUT01 | prostate tumor, 50 M, match to PROSNOT02 | 1 | 0.0310 |
| LUNGTUT03 | lung tumor, 69 M, match to LUNGNOT15 | 1 | 0.0308 |
| BLADTUT02 | bladder tumor, 80 F, match to BLADNOT03 | 1 | 0.0305 |
| BRAITUT08 | brain tumor, astrocytoma, 47 M | 2 | 0.0293 |
| PROSTUT12 | prostate tumor, 65 M, match to PROSNOT20 | 1 | 0.0279 |
| BLADNOT04 | bladder, 28 M | 1 | 0.0278 |
| TESTTUT02 | testicular tumor, 31 M | 1 | 0.0278 |
| THYRNOT03 | thyroid tumor, adenoma, 28 F | 2 | 0.0277 |
| SINTNOT13 | small intestine, ileum, ulcerative cholitis, 25 F | 1 | 0.0275 |
| COLNTUT03 | colon tumor, 62 M, match to COLNNOT16 | 1 | 0.0272 |
| BLADTUT05 | bladder tumor, 66 M, match to BLADNOT06 | 1 | 0.0268 |
| KIDNTUT01 | kidney tumor, Wilms, 8m F | 1 | 0.0267 |
| PENITUT01 | penis tumor, carcinoma, 64 M | 1 | 0.0267 |
| COLNNOT23 | colon, 16 M | 1 | 0.0264 |
| BRAITUT13 | brain tumor, meningioma, 68 M | 1 | 0.0262 |

FIGURE 4A

| | | |
|---|---|---|
| LIVRTUT01 | liver tumor, metastasis, 51 F | 1 | 0.0259 |
| PROSNOT14 | prostate, 60 M, match to PROSTUT08 | 1 | 0.0256 |
| BRSTTUT08 | breast tumor, 45 F, match to BRSTNOT09 | 1 | 0.0254 |
| BMARNOT03 | bone marrow, 16 M | 1 | 0.0242 |
| RATRNOT02 | heart, right atrium, 39 M | 1 | 0.0236 |
| PANCNOT01 | pancreas, 29 M | 1 | 0.0214 |
| LUNGNOT04 | lung, 2 M | 1 | 0.0183 |
| SYNORAT04 | synovium, wrist, rheumatoid, 62 F | 1 | 0.0174 |
| PLACNOT02 | placenta, fetal F | 1 | 0.0168 |
| BRSTNOT03 | breast, 54 F, match to BRSTTUT02 | 1 | 0.0147 |
| SPLNNOT04 | spleen, 2 M | 1 | 0.0128 |
| PROSNOT06 | prostate, 57 M, match to PROSTUT04 | 1 | 0.0114 |
| LUNGFET03 | lung, fetal F | 1 | 0.0091 |

Electronic Northern Results returned a total of 36 row(s).

FIGURE 4B

```
  1   M------------------------------EAQAQGLLETEPLQG  SEQ ID NO-1
  1   M------------------------------DRGEQGLLRTDPVPE  SEQ ID NO-5
  1   MPKGNKKPNEKKEELEKFAKELQGSDSDEDAVVIEQPTVE         SEQ ID NO-6

17   TD-EDAVASADFSSMLSEEEKEELKAELVQLEDEITTLRQ         SEQ ID NO-1
 17   EG-EDVAATISATETLSEEEQEELRRELAKVEEEIQTLSQ         SEQ ID NO-5
 41   PKLPQNDSSSNKIVLSQAEKDLLRTELDKTEEEISTLKQ          SEQ ID NO-6

56   VLSAKERHLVEIKQKLGMNLMNELKQNFSKSWHDMQTTTA         SEQ ID NO-1
 56   VLAAKEKHLAEIKRRKLGINSLQELKQNIAKGWQDVTATSA        SEQ ID NO-5
 81   VLSARQKHAAELKRRKLGLTPFSELSQDINRSLKTVTDTDA        SEQ ID NO-6

96   YKKTHETLSHAGQKATAAF------------SNVGTA            SEQ ID NO-1
 96   YKKTSETLSQAGQKASAAF------------SSVGSV            SEQ ID NO-5
121   CTHFIEINIQKKKKQSMYYIKRLSKNIQTVPILTSEKKRI         SEQ ID NO-6

121   ---ISKKFGDMS---------------Y------              SEQ ID NO-1
121   ---ITKKLED-----------------------               SEQ ID NO-5
161   LHAFIVLKKKSSILKSLLLWQQYQKTAEVAAATSDTVKEK         SEQ ID NO-6

141   --MRNSPTFKSFEERVETTVTSLKTKVGGTNPNGGSFEE          SEQ ID NO-1
128   --VKNSPTFKSFEEKVE----NLKSKVGGTKPAGGDFGE          SEQ ID NO-5
201   WNDMRNSSLFKSFESKLGSALNN--AKMAASTSI---D           SEQ ID NO-6

178   VLSSTAHASAQSLAGGSRRTKEEELQC                     SEQ ID NO-1
161   VLNSAANASATTEPLPEKT-QESL                         SEQ ID NO-5
234   HLAGAARGPSQTGTPVAEEAKPIS                         SEQ ID NO-6
```

FIGURE 5

```
  1 M T L F H F G N C F A L A Y F P Y F I T Y K C S G L S E Y N A F W K C V Q A G V   SEQ ID NO-3
  1 M S F F H F I N C F A L A F A P Y F I V Y K Y S G I N E Y S S I W K C A T A S G   SEQ ID NO-7

41 T Y L F V Q L C K M L F L A T F F P T W E G G I Y D F I G E F M K A S V D V A D   SEQ ID NO-3
 41 G Y L L T Q L A K L L I A T F F P A L D S E G F S I V P E F L K S S A D I I D   SEQ ID NO-7

81 L I G L N L V M S R - N A G K G E Y K I M V A A L G W A T A E L I M S R C I P L   SEQ ID NO-3
 81 V I G L H L L L M T N F L A G K G E V R F V V G G L G W F A H S V A H R L V L L   SEQ ID NO-7

120 W V G A R G I E F D W K Y I Q M S I D S N I S L V H Y I V A S A Q V W M I T R Y   SEQ ID NO-3
121 W V G A R G T A F T W R W V Q T S L D S S A D L L V I V S L A C L T W M I T R -   SEQ ID NO-7

160 D L Y H N F R P A V L L L M F L S V Y K A F V M E T F V H L C S L G S W A R L D   SEQ ID NO-3
160 - - - T P N K F L V S - - P I L A I T V Q H T E F - - - S L Y G W S L L A       SEQ ID NO-7

200 A R - - - A V V T G L L A L K H F G P V C R R C Q C A L L G L V S Q T L M Y L F   SEQ ID NO-3
188 F R F A Y S I A T A I L T V V V Y S A - - N R T A S T R K N - - - - - - -       SEQ ID NO-7

237 P A S L Q V L V K       SEQ ID NO-3
216 - - - - - - - - E       SEQ ID NO-7
```

FIGURE 6

TUMOR PROTEINS

This application is a divisional application of U.S. application Ser. No. 08/715,204, filed Sep. 17, 1996, now U.S. Pat. No. 5,874,286.

FIELD OF THE INVENTION

The present invention relates to nucleic acid and amino acid sequences of novel human tumor proteins and to the use of these sequences in the diagnosis, study, prevention, and treatment of diseases.

BACKGROUND OF THE INVENTION

In an effort to identify genes involved in the early stages of tumor progression, Bryne J A et al (1995, Cancer Res 55: 2896–2903) screened human breast and basal cell carcinomas for genes commonly overexpressed in tumor cells relative to non-tumor tissue. One novel sequence, D52, was differentially expressed in carcinoma cells and showed little homology to other genes. Chen S L et al (1996, Oncogene 12: 741–751) independently cloned D52 based on its increased expression in lung tumor derived cell lines relative to cell lines derived from normal tissues. Recently, Byrne et al (1996, Genomics 35: 523–532) described a human homolog of D52, termed D53, which is often coexpressed with D52 and may form hetero- or homo-dimers. Both D52 and D53 contain PEST domains, regions that are rich in amino acid residues proline (P), glutamate (E), serine (S), and threonine (T) (Rechsteiner M (1990) Semin Cell Biol 1: 433–440). In human D52, 18 of 37 amino terminal residues are PEST domain residues (Byrne et al, supra). PEST domains are associated with rapidly degraded enzymes, transcriptional factors, and components of receptor signaling pathways (Loetscher P et al (1991) J Biol Chem 266: 11213–11220). *Caenorhabditis elegans* open reading frame (ORF) F13E6.1 has homology to D52 (Wilson R et al (1994) Nature 368: 32–38).

Tumor Proteins and Disease

Cancer remains a major public health concern, and current preventative measures and treatments do not match the needs of most patients. For example, among women in the United States, as many as one in eight will contract breast cancer in their lifetime (Helzlsouer K J (1994) Curr Opin Oncol 6: 541–548). Furthermore, the incidence of breast cancer is rising by about 1% a year (Harris J R et al (1992) N Engl J Med 327: 319–328). Among men over 50 years of age, the lifetime risk of prostate cancer is 9.5% and of death from prostate cancer is 2.9% (McLellan D L et al (1995) Can Med Assoc J 153: 895–900).

Genes may be differentially expressed in tumor cells relative to non-tumor cells. For example, elevated expression levels of 12-lipooxygenase correlate with advanced stage and poor differentiation of human prostate cancer (Gao X et al (1995) Urology 46: 227–237). Additionally, the high incidence of HER2 gene overexpression in breast tumors suggests that perturbations in HER2 are among the earliest and most common genetic lesions in human breast cancer (Liu E et al (1992) Oncogene 7: 1027–1032). This correlation has led to the development of potential HER2 specific therapeutics (Kern J A et al (1993) Am J Respir Cell Mol Biol).

The discovery of additional tumor associated genes may provide agents which are more efficacious in cancer diagnosis and treatment than HER2 and 12-lipooxygenase. Novel tumor associated genes may be specific to a different spectrum of tumor types than known genes. A new tumor protein would satisfy a significant need in the art by providing new agents for the diagnosis, prevention, and treatment of cancer.

SUMMARY

The present invention discloses two novel human tumor proteins (hereinafter referred to individually as TUPROA and TUPROB, and collectively as TUPRO), characterized as having homology to human D52 (GI 790225). and *C. elegans* ORF ZK418.5 (GI 470373), respectively. Accordingly, the invention features substantially purified tumor proteins, as shown the in amino acid sequence of SEQ ID NO:1 and SEQ ID NO:3 and having characteristics of tumor proteins.

One aspect of the invention features isolated and substantially purified polynucleotides which encode TUPRO. In a particular aspect, the polynucleotides are the nucleotide sequences of SEQ ID NO:2 and SEQ ID NO:4. In addition, the invention features polynucleotide sequences that hybridize under stringent conditions to SEQ ID NO:2 or SEQ ID NO:4.

The invention further relates to nucleic acid sequences encoding TUPRO, oligonucleotides, peptide nucleic acids (PNA), fragments, portions or antisense molecules thereof, methods for producing TUPRO or fragments thereof, and use of the sequences in expression vectors and host cells comprising polynucleotides which encode TUPRO. The present invention also relates to antibodies which bind specifically to TUPRO and pharmaceutical compositions comprising substantially purified TUPRO or fragments thereof, or antagonists of TUPRO.

BRIEF DESCRIPTION OF THE FIGURES

FIGS. 1A, 1B and 1C show trip amino acid sequence (SEQ ID NO:1) and nucleic acid sequence (SEQ ID NO:2) of the novel tumor protein, TUPROA. The alignment was produced using MACDNASIS software (Hitachi Software Engineering Co Ltd, San Bruno Calif.).

FIGS. 2A, 2B and 2C show the amino acid sequence (SEQ ID NO:3) and nucleic acid sequence (SEQ ID NO:4) of the novel tumor protein, TUPROB.

FIG. 3 shows the northern analysis for SEQ ID NO:2. The northern analysis was produced electronically using The Life SEQ database (Incyte Pharmaceuticals, Palo Alto Calif.).

FIGS. 4A and 4B shows the northern analysis for SEQ ID NO:4.

FIG. 5 shows the amino acid sequence alignments among TUPROA (SEQ ID NO:1), human D52 (GI 790225; SEQ ID NO:5), and *C. elegans* F13E6.1 (GI 1072344; SEQ ID NO:6). The alignment was produced using the multisequence alignment program of DNASTAR software (DNAStar Inc, Madison Wis,).

FIG. 6 shows the amino acid sequence alignments between TUPROB (SEQ ID NO:3) and *C. elegans* ORF ZK418.5 (GI 470373; SEQ ID NO:6).

DETAILED DESCRIPTION OF THE INVENTION

Figure 7:
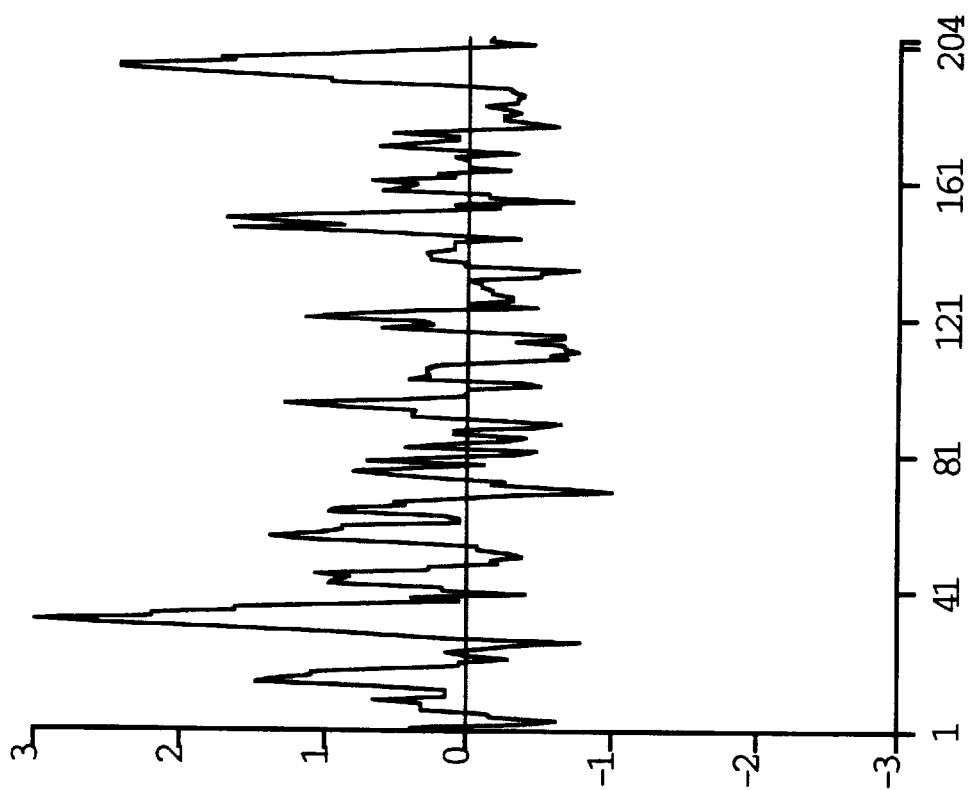
FIG. 7 shows the hydrophobicity plot (generated using MacDNAsis software) for TUPROA, SEQ ID NO:1; the X axis reflects amino acid position, and the y axis reflects, hydrophobicity FIGS. 7, 8, 9 and 10.

Definitions "Nucleic acid sequence" as used herein refers to an oligonucleotide, nucleotide or polynucleotide, and fragments or portions thereof, and to DNA or RNA of genomic or synthetic origin which may be single- or double-stranded, and represent the sense or antisense strand. Similarly, amino acid sequence as used herein refers to oligopeptide or protein sequence.

"Consensus" as used herein may refer to a nucleic acid sequence 1) which has been resequenced to resolve uncalled bases, 2) which has been extended using XL-PCR (Perkin Elmer) in the 5' or the 3' direction and resequenced, 3) which has been assembled from the overlapping sequences of more than one Incyte clone GCG fragment assembly system, (GCG, Madison Wis.), or 4) which has been both extended and assembled.

"Peptide nucleic acid" as used herein refers to a molecule which comprises an oligomer to which an amino acid residue, such as lysine, and an amino group have been added. These small molecules, also designated anti-gene agents, stop transcript elongation by binding to their complementary (template) strand of nucleic acid (Nielsen P E et al (1993) *Anticancer Drug Des* 8:53–63).

As used herein, TUPRO refers to the amino acid sequences of substantially purified TUPRO obtained from any species, particularly mammalian, including bovine, ovine, porcine, murine, equine, and preferably human, from any source whether natural, synthetic, semi-synthetic or recombinant.

A "variant" of TUPRO is defined as an amino acid sequence that is altered by one or more amino acids. The variant may have "conservative" changes, wherein a substituted amino acid has similar structural or chemical properties, eg, replacement of leucine with isoleucine. More rarely, a variant may have "nonconservative" changes, eg, replacement of a glycine with a tryptophan. Similar minor variations may also include amino acid deletions or insertions, or both. Guidance in determining which and how many amino acid residues may be substituted, inserted or deleted without abolishing biological or immunological activity may be found using computer programs well known in the art, for example, DNASTAR software.

A "deletion" is defined as a change in either amino acid or nucleotide sequence in which one or more amino acid or nucleotide residues, respectively, are absent.

An "insertion" or "addition" is that change in an amino acid or nucleotide sequence which has resulted in the addition of one or more amino acid or nucleotide residues, respectively, as compared to the naturally occurring TUPRO.

A "substitution" results from the replacement of one or more amino acids or nucleotides by different amino acids or nucleotides, respectively.

The term "biologically active" refers to a TUPRO having structural, regulatory or biochemical functions of a naturally occurring TUPRO. Likewise, "immunologically active" defines the capability of the natural, recombinant or synthetic TUPRO, or any oligopeptide thereof, to induce a specific immune response in appropriate animals or cells and to bind with specific antibodies.

The term "derivative" as used herein refers to the chemical modification of a nucleic acid encoding TUPRO or the encoded TUPRO. Illustrative of such modifications would be replacement of hydrogen by an alkyl, acyl, or amino group. A nucleic acid derivative would encode a polypeptide which retains essential biological characteristics of natural TUPRO.

As used herein, the term "substantially purified" refers to molecules, either nucleic or amino acid sequences, that are removed from their natural environment, isolated or separated, and are at least 60% free, preferably 75% free, and most preferably 90% free from other components with which they are naturally associated.

"Stringency" typically occurs in a range from about Tm–5° C. (5° C. below the Tm of the probe) to about 20° C. to 25° C. below Tm. As will be understood by those of skill in the art, a stringency hybridization can be used to identify or detect identical polynucleotide sequences or to identify or detect similar or related polynucleotide sequences.

The term "hybridization" as used herein shall include "any process by which a strand of nucleic acid joins with a complementary strand through base pairing" (Coombs J (1994) *Dictionary of Biotechnology*, Stockton Press, New York N.Y.). Amplification as carried out in the polymerase chain reaction technologies is described in Dieffenbach C W and G S Dveksler (1995, *PCR Primer, a Laboratory Manual*, Cold Spring Harbor Press, Plainview N.Y.).

Preferred Embodiments

The present invention relates to novel human tumor proteins and to the use of the nucleic acid and amino acid sequences in the study, diagnosis, prevention and treatment of disease. The sequences encoding TUPRO were found in cDNA libraries from a variety of tissues including several types of tumors FIGS. 3 and 4A, and 4B. TUPROB expression is strongly associated with cDNA libraries derived from tumor tissue (FIG. 4).

The present invention also encompasses TUPRO variants. A preferred TUPRO variant is one having at least 80% amino acid sequence similarity to the TUPRO amino acid sequence (SEQ ID NO:1 or SEQ ID NO:3), a more preferred TUPRO variant is one having at least 90% amino acid sequence similarity to SEQ ID NO:1 or SEQ ID NO:3, and a most preferred TUPRO variant is one having at least 95% amino acid sequence similarity to SEQ ID NO:1 or SEQ ID NO:3.

Nucleic acids encoding the human tumor protein TUPROA of the present invention were first identified in cDNA, Incyte Clone 146723 from a cDNA library made from peripheral blood mononuclear cells, TLYMNOR01, through a computer-generated search for amino acid sequence alignments. The following Incyte clones (and cDNA libraries from which they were derived) were extended and assembled to create the consensus sequence (SEQ ID NO:2): 146723 (TLYMNOR01); 763607 (BRAITUT02); and 601581 (BRSTNOT02). TUPROA, SEQ ID NO:1, is encoded by the nucleic acid sequence of SEQ ID NO:2.

TUPROB was first identified in cDNA, Incyte clone 717832 from a cDNA library made from prostate tumor tissue, PROSTUT01. The following Incyte clones (and cDNA libraries from which they were derived) were extended and assembled to create the consensus sequence (SEQ ID NO:4): 717832 (PROSTUT01); 274790 (PANCDIT03 ); 628576 (KIDNOT05); 890214 (STOMTUT01); 985743 (LVENNOT03); 1321834 (BLADNOT04); 1398242 (BRAITUT08); and 1733437 (BRSTTUT08). TUPROB, SEQ ID NO:3, is encoded by the nucleic acid sequence of SEQ ID NO:4.

Figure 8:
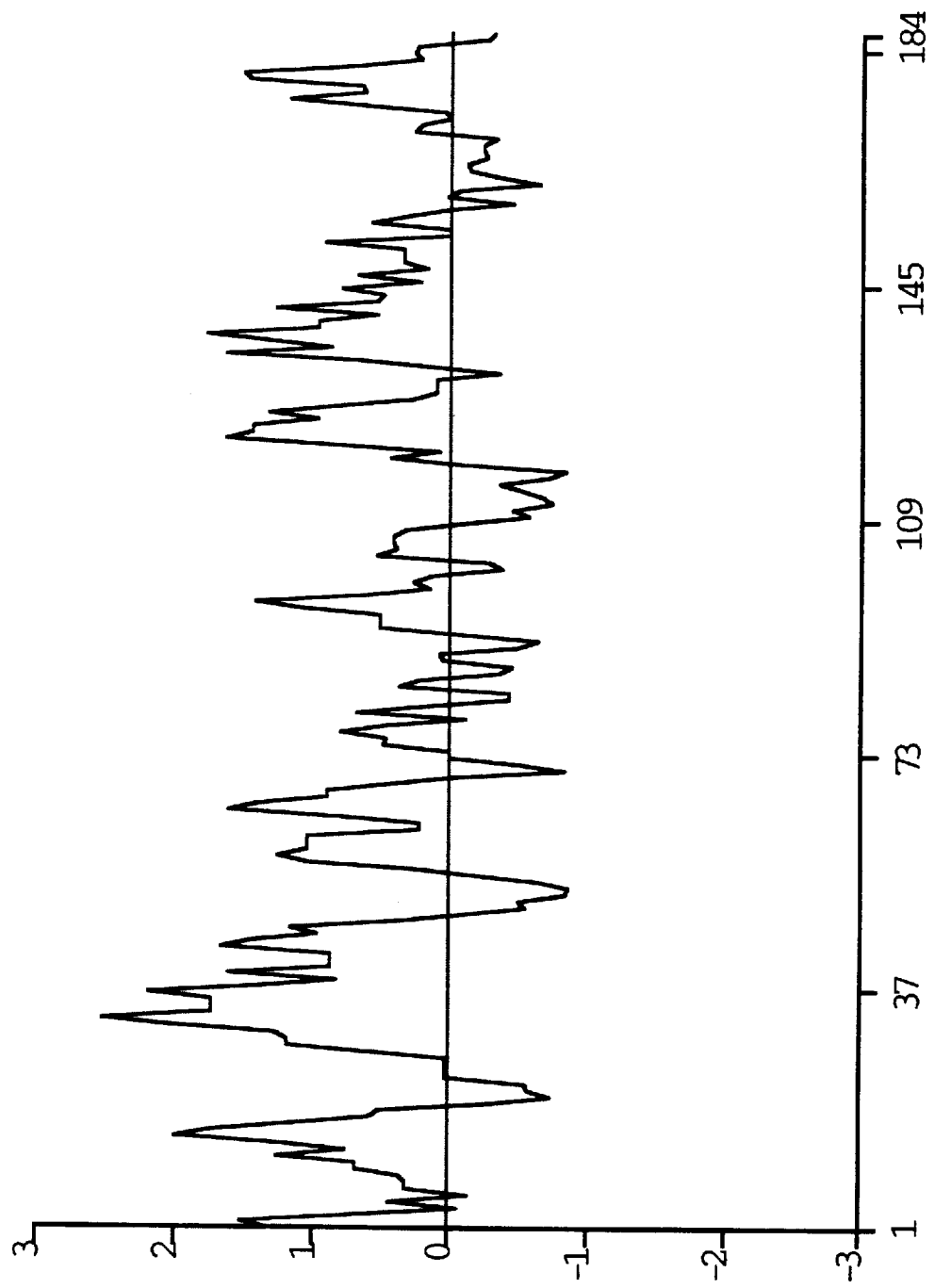
FIG. 8 shows the hydrophobicity plot for human D52, SEQ ID NO:5.
Figure 9:
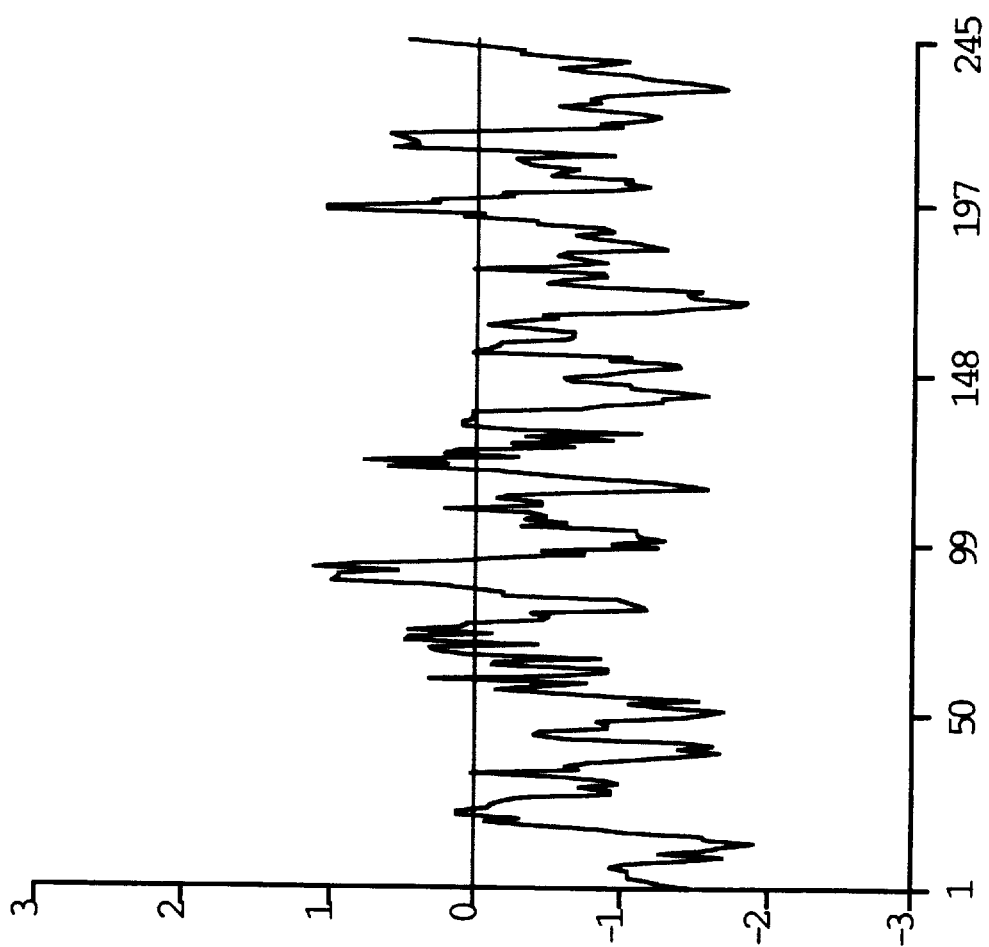
FIG. 9 shows the hydrophobicity plot for TUPROB, SEQ ID NO:3.
Figure 10:
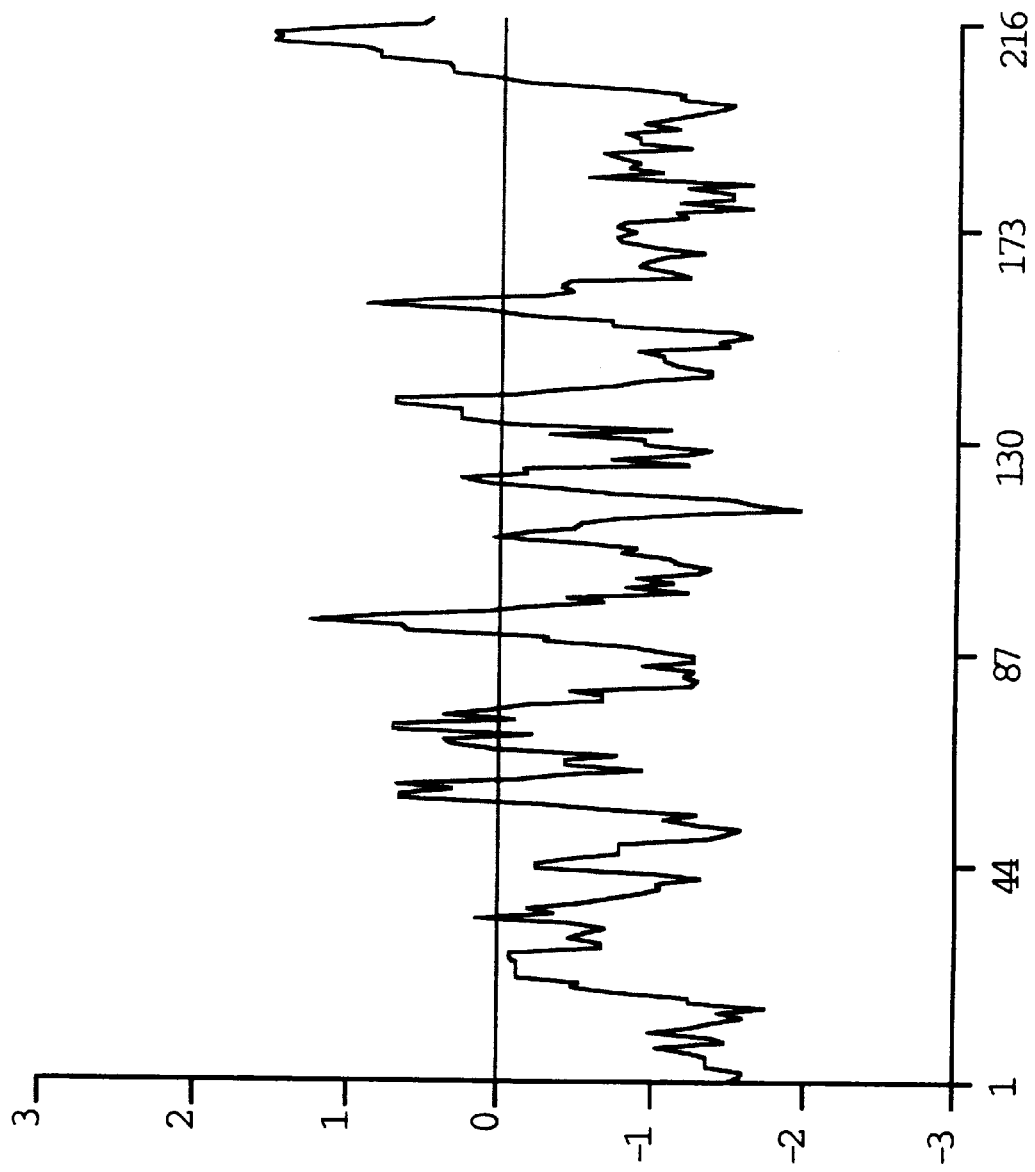
FIG. 10 shows the hydrophobicity plot for *C. elegans* ORF ZK418.5, SEQ ID NO:7.

The present invention is based, in part, on the chemical and structural homology among TUPROA, human D52 (GI 790225; Byrne et al, supra), and *C. elegans* F13E6.1 (GI 1072344; Wilson et al, supra; FIG. 5). The present invention is also based, in part, on the chemical and structural homology between TUPROB and *C. elegans* ORF ZK418.5 (GI 470373; Wilson et al, supra) FIG. 6). The novel TUPROA is 204 amino acids long and shares 52% identity with human D52. The novel TUPROB is 245 amino acids long and shares 40% identity with *C. elegans* ORF ZK418.5. As illustrated by FIGS. 7 and 8, TUPROA and human D52 have similar hydrophobicity plots suggesting similar structure. TUPROB and *C. elegans* ORF ZK418.5 have similar hydrophobicity plots suggesting membrane localization (FIGS. 9 and 10). TUPROA and TUPROB each have one potential N-glycosylation site.

The TUPRO Coding Sequences

The nucleic acid and deduced amino acid sequences of TUPROA and TUPROB are shown in FIGS. 1A, 1B, 1C, 2A, 2B, and 2C. In accordance with the invention, any nucleic acid sequence which encodes the amino acid sequence of TUPRO can be used to generate recombinant molecules which express TUPRO. In a specific embodiment described herein, a nucleotide sequence encoding a portion of TUPROA was first isolated as Incyte Clone 146723 from a peripheral blood mononuclear cell cDNA library (TLYMNOR01). In another specific embodiment described herein, a nucleotide sequence encoding a portion of TUPROB was first isolated as Incyte Clone 717832 from a cDNA library made from prostate tumor tissue, PROSTUT01.

It will be appreciated by those skilled in the art that as a result of the degeneracy of the genetic code, a multitude of TUPRO-encoding nucleotide sequences, some bearing minimal homology to the nucleotide sequences of any known and naturally occurring gene may be produced. The invention contemplates each and every possible variation of nucleotide sequence that could be made by selecting combinations based on possible codon choices. These combinations are made in accordance with the standard triplet genetic code as applied to the nucleotide sequence of naturally occurring TUPRO, and all such variations are to be considered as being specifically disclosed.

Although nucleotide sequences which encode TUPRO and its variants are preferably capable of hybridizing to the nucleotide sequence of the naturally occurring TUPRO under appropriately selected conditions of stringency, it may be advantageous to produce nucleotide sequences encoding TUPRO or its derivatives possessing a substantially different codon usage. Codons may be selected to increase the rate at which expression of the peptide occurs in a particular prokaryotic or eukaryotic expression host in accordance with the frequency with which particular codons are utilized by the host. Other reasons for substantially altering the nucleotide sequence encoding TUPRO and its derivatives without altering the encoded amino acid sequences include the production of RNA transcripts having more desirable properties, such as a greater half-life, than transcripts produced from the naturally occurring sequence.

It is now possible to produce a DNA sequence, or portions thereof, encoding a TUPRO and its derivatives entirely by synthetic chemistry, after which the synthetic gene may be inserted into any of the many available DNA vectors and cell systems using reagents that are well known in the art at the time of the filing of this application. Moreover, synthetic chemistry may be used to introduce mutations into a sequence encoding TUPRO or any portion thereof.

Also included within the scope of the present invention are polynucleotide sequences that are capable of hybridizing to the nucleotide sequence of FIGS. 1A, 1B, 1C, 2A, 2B, and 2C under various conditions of stringency. Hybridization conditions are based on the melting temperature (Tm) of the nucleic acid binding complex or probe, as taught in Berger and Kimmel (1987, *Guide to Molecular Cloning Technicues, Methods in Enzymology*, Vol 152, Academic Press, San Diego Calif.) incorporated herein by reference, and may be used at a defined stringency.

Altered nucleic acid sequences encoding TUPRO which may be used in accordance with the invention include deletions, insertions or substitutions of different nucleotides resulting in a polynucleotide that encodes the same or a functionally equivalent TUPRO. The protein may also show deletions, insertions or substitutions of amino acid residues which produce a silent change and result in a functionally equivalent TUPRO. Deliberate amino acid substitutions may be made on the basis of similarity in polarity, charge, solubility, hydrophobicity, hydrophilicity, and/or the amphipathic nature of the residues as long as the biological activity of TUPRO is retained. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine phenylalanine, and tyrosine.

Included within the scope of the present invention are alleles of TUPRO. As used herein, an "allele" or "allelic sequence" is an alternative form of TUPRO. Alleles result from a mutation, ie, a change in the nucleic acid sequence, and generally produce altered mRNAs or polypeptides whose structure or function may or may not be altered. Any given gene may have none, one or many allelic forms. Common mutational changes which give rise to alleles are generally ascribed to natural deletions, additions or substitutions of amino acids. Each of these types of changes may occur alone, or in combination with the others, one or more times in a given sequence.

Methods for DNA sequencing are well known in the art and employ such enzymes as the Klenow fragment of DNA polymerase I, SEQUENASE (US Biochemical Corp, Cleveland Ohio)), Taq polymerase (Perkin Elmer, Norwalk Conn.), thermostable T7 polymerase (Amersham, Chicago Ill.), or combinations of recombinant polymerases and proofreading exonucleases such as the ELONGASE amplification system marketed by Gibco BRL (Gaithersburg Md.). Preferably, the process is automated with machines such as the Hamilton MICROLAB 2200 (Hamilton, Reno Nev.), Peltier thermal cycler (PTC200; MJ Research, Watertown Mass.) and the ABI 377 DNA sequencers (Perkin Elmer).

Extending the Polynucleotide Sequence

The polynucleotide sequence encoding TUPRO may be extended utilizing partial nucleotide sequence and various methods known in the art to detect upstream sequences such as promoters and regulatory elements. Gobinda et al (1993; PCR Methods Applic 2:318–22) disclose "restriction-site" polymerase chain reaction (PCR) as a direct method which uses universal primers to retrieve unknown sequence adjacent to a known locus. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia T et al (1988) Nucleic Acids Res 16:8186). The primers may be designed using OLIGO® 4.06 Primer Analysis Software (1992; National Biosciences Inc, Plymouth Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Capture PCR (Lagerstrom M et al (1991) PCR Methods Applic 1:111–19) is a method for PCR amplification of DNA fragments adjacent to a known sequence in human and yeast artificial chromosome DNA. Capture PCR also requires multiple restriction enzyme digestions and ligations to place an engineered double-stranded sequence into an unknown portion of the DNA molecule before PCR.

Another method which may be used to retrieve unknown sequences is that of Parker J D et al (1991; Nucleic Acids Res 19:3055–60). Additionally, one can use PCR, nested primers and PromoterFinder libraries to walk in genomic DNA (PROMOTERFINDER (Clontech Palo Alto, Calif.). This process avoids the need to screen libraries and is useful in finding intron/exon junctions.

Preferred libraries for screening for full length cDNAs are ones that have been size-selected to include larger cDNAs. Also, random primed libraries are preferred in that they will contain more sequences which contain the 5' and upstream regions of genes. A randomly primed library may be particularly useful if an oligo d(T) library does not yield a full-length cDNA. Genomic libraries are useful for extension into the 5' nontranslated regulatory region.

Capillary electrophoresis may be used to analyze the size or confirm the nucleotide sequence of sequencing or PCR products. Systems for rapid sequencing are available from Perkin Elmer, Beckman Instruments (Fullerton Calif.), and other companies. Capillary sequencing may employ flowable polymers for electrophoretic separation, four different fluorescent dyes (one for each nucleotide) which are laser activated, and detection of the emitted wavelengths by a charge coupled device camera. Output/light intensity is converted to electrical signal using appropriate software (eg. GENOTYPER and SEQUENCE NAVIGATORS from Perkin Elmer) and the entire process from loading of samples to computer analysis and electronic data display is computer controlled. Capillary electrophoresis is particularly suited to the sequencing of small pieces of DNA which might be present in limited amounts in a particular sample. The reproducible sequencing of up to 350 bp of M13 phage DNA in 30 min has been reported (Ruiz-Martinez M C et al (1993) Anal Chem 65:2851–2858).

Expression of the Nucleotide Sequence

In accordance with the present invention, polynucleotide sequences which encode TUPRO, fragments of the polypeptide, fusion proteins or functional equivalents thereof may be used in recombinant DNA molecules that direct the expression of TUPRO in appropriate host cells. Due to the inherent degeneracy of the genetic code, other DNA sequences which encode substantially the same or a functionally equivalent amino acid sequence, may be used to clone and express TUPRO. As will be understood by those of skill in the art, it may be advantageous to produce TUPRO-encoding nucleotide sequences possessing non-naturally occurring codons. Codons preferred by a particular prokaryotic or eukaryotic host (Murray E et al (1989) Nuc Acids Res 17:477–508) can be selected, for example, to increase the rate of TUPRO expression or to produce recombinant RNA transcripts having desirable properties, such as a longer half-life, than transcripts produced from naturally occurring sequence.

The nucleotide sequences of the present invention can be engineered in order to alter a TUPRO coding sequence for a variety of reasons, including but not limited to, alterations which modify the cloning, processing and/or expression of the gene product. For example, mutations may be introduced using techniques which are well known in the art, eg, site-directed mutagenesis to insert new restriction sites, to alter glycosylation patterns, to change codon preference, to produce splice variants, etc.

In another embodiment of the invention, a natural, modified or recombinant polynucleotides encoding TUPRO may be ligated to a heterologous sequence to encode a fusion protein. For example, for screening of peptide libraries for inhibitors of TUPRO activity, it may be useful to encode a chimeric TUPRO protein that is recognized by a commercially available antibody. A fusion protein may also be engineered to contain a cleavage site located between a TUPRO sequence and the heterologous protein sequence, so that the TUPRO may be cleaved and purified away from the heterologous moiety.

In an alternate embodiment of the invention, the coding sequence of TUPRO may be synthesized, whole or in part, using chemical methods well known in the art (see Caruthers M H et al (1980) Nuc Acids Res Symp Ser 215–23, Horn T et al(1980) Nuc Acids Res Symp Ser 225–32, etc). Alternatively, the protein itself could be produced using chemical methods to synthesize a TUPRO amino acid sequence, whole or in part. For example, peptide synthesis can be performed using various solid-phase techniques (Roberge J Y et al (1995) Science 269:202–204) and automated synthesis may be achieved, for example, using the ABI 431A Peptide Synthesizer (Perkin Elmer) in accordance with the instructions provided by the manufacturer.

The newly synthesized peptide can be substantially by preparative high performance liquid chromatography (eg, Creighton (1983) *Proteins, Structures and Molecular Principles*, WH Freeman and Co, New York N.Y.). The composition of the synthetic peptides may be confirmed by amino acid analysis or sequencing (eg, the Edman degradation procedure; Creighton, supra). Additionally the amino acid sequence of TUPRO, or any part thereof, may be altered during direct synthesis and/or combined using chemical methods with sequences from other proteins, or any part thereof, to produce a variant polypeptide.

Expression Systems

In order to express a biologically active TUPRO, the nucleotide sequence encoding TUPRO or its functional equivalent, is inserted into an appropriate expression vector, ie, a vector which contains the necessary elements for the transcription and translation of the inserted coding sequence.

Methods which are well known to those skilled in the art can be used to construct expression vectors containing a TUPRO coding sequence and appropriate transcriptional or translational controls. These methods include in vitro recombinant DNA techniques, synthetic techniques and in vivo recombination or genetic recombination. Such techniques are described in Sambrook et al (1989) *Molecular Cloning, A Laboratory Manual*, Cold Spring Harbor Press, Plainview N.Y. and Ausubel F M et al (1989) *Current Protocols in Molecular Biology*, John Wiley & Sons, New York N.Y.

A variety of expression vector/host systems may be utilized to contain and express a TUPRO coding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (eg, baculovirus); plant cell systems transfected with virus expression vectors (eg, cauliflower mosaic virus, CaMV; tobacco mosaic virus, TMV) or transformed with bacterial expression vectors (eg, Ti or pBR322 plasmid); or animal cell systems.

The "control elements" or "regulatory sequences" of these systems vary in their strength and specificities and are those nontranslated regions of the vector, enhancers, promoters, and 3' untranslated regions, which interact with host cellular proteins to carry out transcription and translation. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla Calif.) or pSport1 (Gibco BRL) and ptrp-lac hybrids and the like may be used. The baculovirus polyhedrin promoter may be used in insect cells. Promoters or enhancers derived from the genomes of plant cells (eg, heat shock, RUBISCO; and storage protein genes) or from plant viruses (eg, viral promoters or leader sequences) may be cloned into the vector. In mammalian cell systems, promoters from the mammalian genes or from mammalian viruses are most appropriate. If it is necessary to generate a cell line that contains multiple copies of TUPRO, vectors based on SV40 or EBV may be used with an appropriate selectable marker.

In bacterial systems, a number of expression vectors may be selected depending upon the use intended for TUPRO. For example, when large quantities of TUPRO are needed for the induction of antibodies, vectors which direct high level expression of fusion proteins that are readily purified may be desirable. Such vectors include, but are not limited to, the multifunctional *E. coli* cloning and expression vectors such as BLUESCRIPT phagemid (Stratagene), in which the TUPRO coding sequence may be ligated into the vector in frame with sequences for the amino-terminal Met and the subsequent 7 residues of β-galactosidase so that a hybrid protein is produced; pIN vectors (Van Heeke & Schuster (1989) J Biol Chem 264:5503–5509); and the like. pGEX vectors (Promega, Madison Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor XA protease cleavage sites so that the cloned polypeptide of interest can be released from the GST moiety at will.

In the yeast, *Saccharomvces cerevisiae*, a number of vectors containing constitutive or inducible promoters such as alpha factor, alcohol oxidase and PGH may be used. For reviews, see Ausubel et al (supra) and Grant et al (1987) Methods in Enzymology 153:516–544.

In cases where plant expression vectors are used, the expression of a sequence encoding TUPRO may be driven by any of a number of promoters. For example, viral promoters such as the 35S and 19S promoters of CaMV (Brisson et al (1984) Nature 310:511–514) may be used alone or in combination with the omega leader sequence from TMV (Takamatsu et al (1987) EMBO J 6:307–311). Alternatively, plant promoters such as the small subunit of RUBISCO (Coruzzi et al (1984) EMBO J 3:1671–1680; Broglie et al (1984) Science 224:838–843); or heat shock promoters (Winter J and Sinibaldi R M (1991) Results Probl Cell Differ 17:85–105) may be used. These constructs can be introduced into plant cells by direct DNA transformation or pathogen-mediated transfection. For reviews of such techniques, see Hobbs S or Murry L E in McGraw Hill *Yearbook of Science and Technology* (1992) McGraw Hill New York N.Y., pp 191–196 or Weissbach and Weissbach (1988) *Methods for Plant Molecular Biology*, Academic Press, New York N.Y., pp 421–463.

An alternative expression system which could be used to express TUPRO is an insect system. In one such system, *Autographa californica* nuclear polyhedrosis virus (AcNPV) is used as a vector to express foreign genes in *Spodoptera frugiperda* cells or in Trichoplusia larvae. The TUPRO coding sequence may be cloned into a nonessential region of the virus, such as the polyhedrin gene, and placed under control of the polyhedrin promoter. Successful insertion of TUPRO will render the polyhedrin gene inactive and produce recombinant virus lacking coat protein coat. The recombinant viruses are then used to infect *S. frugiperda* cells or Trichoplusia larvae in which TUPRO is expressed (Smith et al (1983) J Virol 46:584; Engelhard E K et al (1994) Proc Nat Acad Sci 91:3224–7).

In mammalian host cells, a number of viral-based expression systems may be utilized. In cases where an adenovirus is used as an expression vector, a TUPRO coding sequence may be ligated into an adenovirus transcription/translation complex consisting of the late promoter and tripartite leader sequence. Insertion in a nonessential E1 or E3 region of the viral genome will result in a viable virus capable of expressing TUPRO in infected host cells (Logan and Shenk (1984) Proc Natl Acad Sci 81:3655–59). In addition, transcription enhancers, such as the rous sarcoma virus (RSV) enhancer, may be used to increase expression in mammalian host cells.

Specific initiation signals may also be required for efficient translation of a TUPRO sequence. These signals include the ATG initiation codon and adjacent sequences. In cases where TUPRO, its initiation codon and upstream sequences are inserted into the appropriate expression vector, no additional translational control signals may be needed. However, in cases where only coding sequence, or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (Scharf D et al (1994) Results Probl Cell Differ 20:125–62; Bittner et al (1987) Methods in Enzymol 153:516–544).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, etc have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express TUPRO may be transformed using expression vectors which contain viral origins of replication or endogenous expression elements and a selectable marker gene. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clumps of stably transformed cells can be proliferated using tissue culture techniques appropriate to the cell type.

Any number of selection systems may be used to recover transformed cell lines. These include, but are not limited to, the herpes simplex virus thymidine kinase (Wigler M et al (1977) Cell 11:223–32) and adenine phosphoribosyltransferase (Lowy I et al (1980) Cell 22:817–23) genes which can be employed in tk- or aprt- cells, respectively. Also, antimetabolite, antibiotic or herbicide resistance can be used as the basis for selection; for example, dhfr which confers resistance to methotrexate (Wigler M et al (1980) Proc Natl Acad Sci 77:3567–70); npt, which confers resistance to the aminoglycosides neomycin and G-418 (Colbere-Garapin F et al (1981) J Mol Biol 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman S C and R C Mulligan (1988) Proc Natl Acad Sci 85:8047–51). Recently, the use of visible markers has gained popularity with such markers as anthocyanins, β glucuronidase and its substrate, GUS, and luciferase and its substrate, luciferin, being widely used not only to identify transformants, but also to quantify the amount of transient or stable protein expression attributable to a specific vector system (Rhodes C A et al (1995) Methods Mol Biol 55:121–131).

Identification of Transformants Containing the Polynucleotide Sequence

Although the presence/absence of marker gene expression suggests that the gene of interest is also present, its presence and expression should be confirmed. For example, if the TUPRO is inserted within a marker gene sequence, recombinant cells containing TUPRO can be identified by the absence of marker gene function. Alternatively, a marker gene can be placed in tandem with a TUPRO sequence under the control of a single promoter. Expression of the marker gene in response to induction or selection usually indicates expression of the tandem TUPRO as well.

Alternatively, host cells which contain the coding sequence for TUPRO and express TUPRO may be identified by a variety of procedures known to those of skill in the art. These procedures include, but are not limited to, DNA-DNA or DNA-RNA hybridization and protein bioassay or immunoassay techniques which include membrane, solution, or chip based technologies for the detection and/or quantification of the nucleic acid or protein.

The presence of the polynucleotide sequence encoding TUPRO can be detected by DNA-DNA or DNA-RNA hybridization or amplification using probes, portions or fragments of polynucleotides encoding TUPRO. Nucleic acid amplification based assays involve the use of oligonucleotides or oligomers based on the TUPRO-encoding sequence to detect transformants containing DNA or RNA encoding TUPRO. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides which can be used as a probe or amplimer.

A variety of protocols for detecting and measuring the expression of TUPRO, using either polyclonal or monoclonal antibodies specific for the protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on TUPRO is preferred, but a competitive binding assay may be employed. These and other assays are described, among other places, in Hampton R et al (1990, *Serological Methods, a Laboratory Manual*, APS Press, St Paul Minn.) and Maddox D E et al (1983, J Exp Med 158:1211).

A wide variety of labels and conjugation techniques are known by those skilled in the art and can be used in various nucleic acid and amino acid assays. Means for producing labeled hybridization or PCR probes for detecting sequences related to polynucleotides encoding TUPRO include oligolabeling, nick translation, end-labeling or PCR amplification using a labeled nucleotide. Alternatively, the TUPRO sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway N.J.), Promega (Madison Wis.), and US Biochemical Corp (Cleveland Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277, 437; 4,275,149 and 4,366,241. Also, recombinant immunoglobulins may be produced as shown in U.S. Pat. No. 4,816,567 incorporated herein by reference.

Purification of TUPRO

Host cells transformed with a nucleotide sequence encoding TUPRO may be cultured under conditions suitable for the expression and recovery of the encoded protein from cell culture. The protein produced by a recombinant cell may be secreted or contained intracellularly depending on the sequence and/or the vector used. As will be understood by those of skill in the art, expression vectors containing polynucleotides encoding TUPRO can be designed with signal sequences which direct secretion of TUPRO through a prokaryotic or eukaryotic cell membrane. Other recombinant constructions may join TUPRO to nucleotide sequence encoding a polypeptide domain which will facilitate purification of soluble proteins (Kroll D J et al (1993) DNA Cell Biol 12:441–53; cf discussion of vectors infra containing fusion proteins).

TUPRO may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor XA or enterokinase (Invitrogen, San Diego Calif.) between the purification domain and TUPRO is useful to facilitate purification. One such expression vector provides for expression of a fusion protein compromising a TUPRO and contains nucleic acid encoding 6 histidine residues followed by thioredoxin and an enterokinase cleavage site. The histidine residues facilitate purification on IMIAC (immobilized metal ion affinity chromatography as described in Porath et al (1992) Protein Expression and Purification 3: 263–281) while the enterokinase cleavage site provides a means for purifying TUPRO from the fusion protein.

In addition to recombinant production, fragments of TUPRO may be produced by direct peptide synthesis using solid-phase techniques (cf Stewart et al (1969) *Solid-Phase Peptide Synthesis*, WH Freeman Co, San Francisco; Merrifield J (1963) J Am Chem Soc 85:2149–2154). In vitro protein synthesis may be performed using manual techniques or by automation. Automated synthesis may be achieved, for example, using Applied Biosystems 431A Peptide Synthesizer (Perkin Elmer, Foster City Calif.) in accordance with the instructions provided by the manufacturer. Various fragments of TUPRO may be chemically synthesized separately and combined using chemical methods to produce the full length molecule.

Uses of TUPRO and Polynucleotides Encoding TUPRO

The rationale for use of the novel nucleotide and polypeptide sequences disclosed herein is based in part on the chemical and structural homology among TUPROA, human tumor protein D52 (GI 790225; Byrne et al, supra), and *C. elegans* F13E6.1 (GI 1072344; Wilson et al, supra) and between TUPROB and *C. elegans* ORF ZK418.5 (GI 470373; Wilson et al, supra). In addition, northern analysis disclosed herein indicates that TUPRO molecules are expressed in cells or tissue derived from many types of human cancer (FIGS. 3, 4A, and 4B).

Mutations in tumor genes are very often found in human tumors and in many instances are thought to be critical to both the initiation of tumor development and to the tumor's ability to survive chemotherapy. Tumor proteins may be essential for tumor development or may enable tumors to withstand chemotherapy. They are therefore potential targets for novel diagnostics and therapeutics. Accordingly, the novel tumor protein TUPRO or a TUPRO derivative, may be used to diagnose, prevent, or treat cancer. In conditions where TUPRO protein activity is not desirable, cells could be treated with an antagonist of TUPRO. Thus, TUPRO antagonists may be used to inactivate TUPRO-specific tumor processes.

TUPRO Antibodies

TUPRO-specific antibodies are useful for the diagnosis of conditions and diseases associated with expression of TUPRO. Such antibodies may include, but are not limited to, polyclonal, monoclonal, chimeric, single chain, Fab fragments and fragments produced by a Fab expression library. Neutralizing antibodies, ie, those which inhibit dimer formation, are especially preferred for diagnostics and therapeutics.

TUPRO for antibody induction does not require biological activity; however, the protein fragment, or oligopeptide must be antigenic. Peptides used to induce specific antibodies may have an amino acid sequence consisting of at least five amino acids, preferably at least 10 amino acids. Preferably, they should mimic a portion of the amino acid sequence of the natural protein and may contain the entire amino acid sequence of a small, naturally occurring molecule. Short stretches of TUPRO amino acids may be fused with those of another protein such as keyhole limpet hemocyanin and antibody produced against the chimeric molecule. Procedures well known in the art can be used for the production of antibodies to TUPRO.

For the production of antibodies, various hosts including goats, rabbits, rats, mice, etc may be immunized by injection with TUPRO or any portion, fragment or oligopeptide which retains immunogenic properties. Depending on the host species, various adjuvants may be used to increase immunological response. Such adjuvants include but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and *Corynebacterium parvum* are potentially useful human adjuvants.

Monoclonal antibodies to TUPRO may be prepared using any technique which provides for the production of antibody molecules by continuous cell lines in culture. These include but are not limited to the hybridoma technique originally described by Koehler and Milstein (1975 Nature 256:495–497), the human B-cell hybridoma technique (Kosbor et al (1983) Immunol Today 4:72; Cote et al (1983) Proc Natl Acad Sci 80:2026–2030) and the EBV-hybridoma technique (Cole et al (1985) *Monoclonal Antibodies and Cancer Therapy*, Alan R Liss Inc, New York N.Y., pp 77–96).

In addition, techniques developed for the production of "chimeric antibodies", the splicing of mouse antibody genes to human antibody genes to obtain a molecule with appropriate antigen specificity and biological activity can be used (Morrison et al (1984) Proc Natl Acad Sci 81:6851–6855; Neuberger et al (1984) Nature 312:604–608; Takeda et al (1985) Nature 314:452–454). Alternatively, techniques described for the production of single chain antibodies (U.S. Pat. No. 4,946,778) can be adapted to produce TUPRO-specific single chain antibodies Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86: 3833–3837), and Winter G and Milstein C (1991; Nature 349:293–299).

Antibody fragments which contain specific binding sites for TUPRO may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse W D et al (1989) Science 256:1275–1281).

A variety of protocols for competitive binding or immunoradiometric assays using either polyclonal or monoclonal antibodies with established specificities are well known in the art. Such immunoassays typically involve the formation of complexes between TUPRO and its specific antibody and the measurement of complex formation. A two-site, monoclonal-based immunoassay utilizing monoclonal antibodies reactive to two noninterfering epitopes on a specific TUPRO protein is preferred, but a competitive binding assay may also be employed. These assays are described in Maddox D E et al (1983, J Exp Med 158:1211).

Diagnostic Assays Using TUPRO Specific Antibodies

Particular TUPRO antibodies are useful for the diagnosis of conditions or diseases characterized by expression of TUPRO or in assays to monitor patients being treated with TUPRO, agonists or inhibitors. Diagnostic assays for TUPRO include methods utilizing the antibody and a label to detect TUPRO in human body fluids or extracts of cells or tissues. The polypeptides and antibodies of the present invention may be used with or without modification. Frequently, the polypeptides and antibodies will be labeled by joining them, either covalently or noncovalently, with a reporter molecule. A wide variety of reporter molecules are known, several of which were described above.

A variety of protocols for measuring TUPRO, using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on TUPRO is preferred, but a competitive binding assay may be employed. These assays are described, among other places, in Maddox, D E et al (1983, J Exp Med 158:1211).

In order to provide a basis for diagnosis, normal or standard values for TUPRO expression must be established. This is accomplished by combining body fluids or cell extracts taken from normal subjects, either animal or human, with antibody to TUPRO under conditions suitable for complex formation which are well known in the art. The amount of standard complex formation may be quantified by comparing various artificial membranes containing known quantities of TUPRO with both control and disease samples from biopsied tissues. Then, standard values obtained from normal samples may be compared with values obtained from samples from subjects potentially affected by disease. Deviation between standard and subject values establishes the presence of disease state.

Drug Screening

TUPRO, its catalytic or immunogenic fragments or oligopeptides thereof, can be used for screening therapeutic compounds in any of a variety of drug screening techniques. The fragment employed in such a test may be free in solution, affixed to a solid support, borne on a cell surface, or located intracellularly. The formation of binding complexes, between TUPRO and the agent being tested, may be measured.

Another technique for drug screening which may be used provides for high throughput screening of compounds having suitable binding affinity to the TUPRO is described in detail in "Determination of Amino Acid Sequence Antigenicity" by Geysen H M, WO Application 84/03564, published on Sep. 13, 1984, and incorporated herein by reference. In summary, large numbers of different small peptide test compounds are synthesized on a solid substrate, such as plastic pins or some other surface. The peptide test compounds are reacted with fragments of TUPRO and washed. Bound TUPRO is then detected by methods well known in the art. Purified TUPRO can also be coated directly onto plates for use in the aforementioned drug screening techniques. Alternatively, non-neutralizing antibodies can be used to capture the peptide and immobilize it on a solid support.

This invention also contemplates the use of competitive drug screening assays in which neutralizing antibodies capable of binding TUPRO specifically compete with a test compound for binding TUPRO. In this manner, the antibodies can be used to detect the presence of any peptide which shares one or more antigenic determinants with TUPRO.

Diagnostic and Therapeutic Uses of the Polynucleotide

A polynucleotide encoding TUPRO, or any part thereof, may be used for diagnostic and/or therapeutic purposes. For diagnostic purposes, polynucleotides encoding TUPRO of this invention may be used to detect and quantitate gene expression in biopsied tissues in which expression of TUPRO may be implicated. The diagnostic assay is useful to distinguish between absence, presence, and excess expression of TUPRO and to monitor regulation of TUPRO levels during therapeutic intervention. Included in the scope of the invention are oligonucleotide sequences, antisense RNA and DNA molecules, and PNAS.

Another aspect of the subject invention is to provide for hybridization or PCR probes which are capable of detecting polynucleotide sequences, including genomic sequences, encoding TUPRO or closely related molecules. The specificity of the probe, whether it is made from a highly specific region, eg, 10 unique nucleotides in the 5' regulatory region, or a less specific region, eg, especially in the 3' region, and the stringency of the hybridization or amplification (maximal, high, intermediate or low) will determine whether the probe identifies only naturally occurring sequences encoding TUPRO, alleles or related sequences.

Probes may also be used for the detection of related sequences and should preferably contain at least 50% of the nucleotides from any of these TUPRO encoding sequences. The hybridization probes of the subject invention may be derived from the nucleotide sequence of SEQ ID NO:2, SEQ ID NO:4, or from genomic sequence including promoter, enhancer elements and introns of the naturally occurring TUPRO. Hybridization probes may be labeled by a variety of reporter groups, including radionuclides such as 32P or 35S, or enzymatic labels such as alkaline phosphatase coupled to the probe via avidin/biotin coupling systems, and the like.

Other means for producing specific hybridization probes for DNAs encoding TUPRO include the cloning of nucleic acid sequences encoding TUPRO or TUPRO derivatives into vectors for the production of MRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides.

Polynucleotide sequences encoding TUPRO may be used for the diagnosis of conditions or diseases with which the expression of TUPRO is associated. For example, polynucleotide sequences encoding TUPRO may be used in hybridization or PCR assays of fluids or tissues from biopsies to detect TUPRO expression. The form of such qualitative or quantitative methods may include Southern or northern analysis, dot blot or other membrane-based technologies; PCR technologies; dip stick, pIN, chip and ELISA technologies. All of these techniques are well known in the art and are the basis of many commercially available diagnostic kits.

The nucleotide sequences encoding TUPRO disclosed herein provide the basis for assays that detect activation or induction associated with cancer. The nucleotide sequence encoding TUPRO may be labeled by methods known in the art and added to a fluid or tissue sample from a patient under conditions suitable for the formation of hybridization complexes. After an incubation period, the sample is washed with a compatible fluid which optionally contains a dye (or other label requiring a developer) if the nucleotide has been labeled with an enzyme. After the compatible fluid is rinsed off, the dye is quantitated and compared with a standard. If the amount of dye in the biopsied or extracted sample is significantly elevated over that of a comparable control sample, the nucleotide sequence has hybridized with nucleotide sequences in the sample, and the presence of elevated levels of nucleotide sequences encoding TUPRO in the sample indicates the presence of the associated disease.

Such assays may also be used to evaluate the efficacy of a particular therapeutic treatment regime in animal studies, in clinical trials, or in monitoring the treatment of an individual patient. In order to provide a basis for the diagnosis of disease, a normal or standard profile for TUPRO expression must be established. This is accomplished by combining body fluids or cell extracts taken from normal subjects, either animal or human, with TUPRO, or a portion thereof, under conditions suitable for hybridization or amplification. Standard hybridization may be quantified by comparing the values obtained for normal subjects with a dilution series of TUPRO run in the same experiment where a known amount of a substantially purified TUPRO is used. Standard values obtained from normal samples may be compared with values obtained from samples from patients afflicted with TUPRO-associated diseases. Deviation between standard and subject values is used to establish the presence of disease.

Once disease is established, a therapeutic agent is administered and a treatment profile is generated. Such assays may be repeated on a regular basis to evaluate whether the values in the profile progress toward or return to the normal or standard pattern. Successive treatment profiles may be used to show the efficacy of treatment over a period of several days or several months.

PCR, as described in U.S. Pat. Nos. 4,683,195 and 4,965,188, provides additional uses for oligonucleotides based upon the TUPRO sequence. Such oligomers are generally chemically synthesized, but they may be generated enzymatically or produced from a recombinant source. Oligomers generally comprise two nucleotide sequences, one with sense orientation (5'→3') and one with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Additionally, methods which may be used to quantitate the expression of a particular molecule include radiolabeling (Melby P C et al 1993 J Immunol Methods 159:235–44) or biotinylating (Duplaa C et al 1993 Anal Biochem 229–36) nucleotides, coamplification of a control nucleic acid, and standard curves onto which the experimental results are interpolated. Quantitation of multiple samples may be speeded up by running the assay in an ELISA format where the oligomer of interest is presented in various dilutions and a spectrophotometric or colorimetric response gives rapid quantitation. For example, the presence of a relatively high amount of TUPRO in extracts of biopsied tissues may indicate the onset of cancer. A definitive diagnosis of this type may allow health professionals to begin aggressive treatment and prevent further worsening of the condition. Similarly, further assays can be used to monitor the progress of a patient during treatment. Furthermore, the nucleotide sequences disclosed herein may be used in molecular biology techniques that have not yet been developed, provided the new techniques rely on properties of nucleotide sequences that are currently known such as the triplet genetic code, specific base pair interactions, and the like.

Based upon its homology to the gene encoding D52, and its expression profile, polynucleotide sequences encoding TUPRO disclosed herein may be useful in the treatment of cancer.

Expression vectors derived from retroviruses, adenovirus, herpes or vaccinia viruses, or from various bacterial plasmids, may be used for delivery of nucleotide sequences to the targeted organ, tissue or cell population. Methods which are well known to those skilled in the art can be used to construct recombinant vectors which will express antisense polynucleotides of the gene encoding TUPRO. See, for example, the techniques described in Sambrook et al (supra) and Ausubel et al (supra).

The polynucleotides comprising full length cDNA sequence and/or its regulatory elements enable researchers to use sequences encoding TUPRO as an investigative tool in sense (Youssoufian H and H F Lodish 1993 Mol Cell Biol 13:98–104) or antisense (Eguchi et al (1991) Annu Rev Biochem 60:631–652) regulation of gene function. Such technology is now well known in the art, and sense or antisense oligomers, or larger fragments, can be designed from various locations along the coding or control regions.

Genes encoding TUPRO can be turned off by transfecting a cell or tissue with expression vectors which express high levels of a desired TUPRO-encoding fragment. Such constructs can flood cells with untranslatable sense or antisense sequences. Even in the absence of integration into the DNA, such vectors may continue to transcribe RNA molecules until all copies are disabled by endogenous nucleases. Transient expression may last for a month or more with a non-replicating vector (Mettler I, personal communication) and even longer if appropriate replication elements are part of the vector system.

As mentioned above, modifications of gene expression can be obtained by designing antisense molecules, DNA, RNA or PNA, to the control regions of gene encoding TUPRO, ie, the promoters, enhancers, and introns. Oligonucleotides derived from the transcription initiation site, eg, between −10 and +10 regions of the leader sequence, are preferred. The antisense molecules may also be designed to block translation of mRNA by preventing the transcript from binding to ribosomes. Similarly, inhibition can be achieved using "triple helix" base-pairing methodology. Triple helix pairing compromises the ability of the double helix to open sufficiently for the binding of polymerases, transcription factors, or regulatory molecules. Recent therapeutic advances using triplex DNA were reviewed by Gee J E et al (In: Huber B E and B I Carr (1994) *Molecular and Immunologic Approaches*, Futura Publishing Co, Mt Kisco N.Y.).

Ribozymes are enzymatic RNA molecules capable of catalyzing the specific cleavage of RNA. The mechanism of ribozyme action involves sequence-specific hybridization of the ribozyme molecule to complementary target RNA, followed by endonucleolytic cleavage. Within the scope of the invention are engineered hammerhead motif ribozyme molecules that can specifically and efficiently catalyze endonucleolytic cleavage of sequences encoding TUPRO.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription of DNA sequences encoding TUPRO. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine and wybutosine as well as acetyl-, methyl-, thio- and similarly modified forms of adenine, cytidine, guanine, thymine, and uridine which are not as easily recognized by endogenous endonucleases.

Methods for introducing vectors into cells or tissues include those methods discussed infra and which are equally suitable for in vivo, in vitro and ex vivo therapy. For ex vivo therapy, vectors are introduced into stem cells taken from the patient and clonally propagated for autologous transplant back into that same patient is presented in U.S. Pat. Nos. 5,399,493 and 5,437,994, disclosed herein by reference. Delivery by transfection and by liposome are quite well known in the art.

Furthermore, the nucleotide sequences for TUPRO disclosed herein may be used in molecular biology techniques that have not yet been developed, provided the new techniques rely on properties of nucleotide sequences that are currently known, including but not limited to such properties as the triplet genetic code and specific base pair interactions.

Detection and Mapping of Related Polynucleotide Sequences

The nucleic acid sequence for TUPRO can also be used to generate hybridization probes for mapping the naturally occurring genomic sequence. The sequence may be mapped to a particular chromosome or to a specific region of the chromosome using well known techniques. These include in situ hybridization to chromosomal spreads, flow-sorted chromosomal preparations, or artificial chromosome constructions such as yeast artificial chromosomes, bacterial artificial chromosomes, bacterial P1 constructions or single chromosome cDNA libraries as reviewed in Price CM (1993; Blood Rev 7:127–34) and Trask B J (1991; Trends Genet 7:149–54).

The technique of fluorescent in situ hybridization of chromosome spreads has been described, among other places, in Verma et al (1988) *Human Chromosomes: A Manual of Basic Techniques*, Pergamon Press, New York N.Y. Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of the gene encoding TUPRO on a physical chromosomal map and a specific disease (or predisposition to a specific disease) may help delimit the region of DNA associated with that genetic disease. The nucleotide sequences of the subject invention may be used to detect differences in gene sequences between normal, carrier or affected individuals.

In situ hybridization of chromosomal preparations and physical mapping techniques such as linkage analysis using established chromosomal markers may be used for extending genetic maps. For example, a sequence tagged site based map of the human genome was recently published by the Whitehead-MIT Center for Genomic Research (Hudson T J et al (1995) Science 270:1945–1954). Often the placement of a gene on the chromosome of another mammalian species such as mouse (Whitehead Institute/MIT Center for Genome Research, Genetic Map of the Mouse, Database Release 10, Apr. 28, 1995) may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome, such as ataxia telangiectasia (AT), has been crudely localized by genetic linkage to a particular genomic region, for example, AT to 11q22–23 (Gatti et al (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier or affected individuals.

Pharmaceutical Compositions

The present invention relates to pharmaceutical compositions which may comprise nucleotides, proteins, antibodies, agonists, antagonists, or inhibitors, alone or in combination with at least one other agent, such as stabilizing compound, which may be administered in any sterile, biocompatible pharmaceutical carrier, including, but not limited to, saline, buffered saline, dextrose, and water. Any of these molecules can be administered to a patient alone, or in combination with other agents, drugs or hormones, in pharmaceutical compositions where it is mixed with excipient(s) or pharmaceutically acceptable carriers. In one embodiment of the present invention, the pharmaceutically acceptable carrier is pharmaceutically inert.

Administration of Pharmaceutical Compositions

Administration of pharmaceutical compositions is accomplished orally or parenterally. Methods of parenteral delivery include topical, intra-arterial (directly to the tumor), intramuscular, subcutaneous, intramedullary, intrathecal, intraventricular, intravenous, intraperitoneal, or intranasal administration. In addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of "Remington's Pharmaceutical Sciences" (Maack Publishing Co, Easton Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores.

Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethylcellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, ie, dosage.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

Manufacture and Storage

The pharmaceutical compositions of the present invention may be manufactured in a manner that known in the art, eg, by means of conventional mixing, dissolving, granulating, dragee-making, levigating, emulsifying, encapsulating, entrapping or lyophilizing processes.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM–50 mM histidine, 0.1%–2% sucrose, 2%–7% mannitol at a pH range of 4.5 to 5.5 that is combined with buffer prior to use.

After pharmaceutical compositions comprising a compound of the invention formulated in a acceptable carrier have been prepared, they can be placed in an appropriate container and labeled for treatment of an indicated condition. For administration of TUPRO, such labeling would include amount, frequency and method of administration.

Therapeutically Effective Dose

Pharmaceutical compositions suitable for use in the present invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, eg, of neoplastic cells, or in animal models, usually mice, rabbits, dogs, or pigs. The animal model is also used to achieve a desirable concentration range and route of administration. Such information can then be used to determine useful doses and routes for administration in humans.

A therapeutically effective dose refers to that amount of protein or its antibodies, antagonists, or inhibitors which ameliorate the symptoms or condition. Therapeutic efficacy and toxicity of such compounds can be determined by standard pharmaceutical procedures in cell cultures or experimental animals, eg, ED50 (the dose therapeutically effective in 50% of the population) and LD50 (the dose lethal to 50% of the population). The dose ratio between therapeutic and toxic effects is the therapeutic index, and it can be expressed as the ratio, ED50/LD50. Pharmaceutical compositions which exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state, eg, tumor size and location; age, weight and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

It is contemplated, for example, that TUPRO or a TUPRO derivative can be delivered in a suitable formulation to stop the progression of cancer.

The examples below are provided to illustrate the subject invention and are not included for the purpose of limiting the invention.

EXAMPLES

I cDNA Library Construction

TLYMNOR01 cDNA Library

The TLYMNOR01 cDNA library was constructed using RNA isolated from non-adherent peripheral blood mononuclear cells obtained from a 24-year-old Caucasian male. The cells were purified on Ficoll Hypaque, then harvested, lysed in GUSCN, and spun through CsCl to obtain RNA for library construction. The RNA was primed with oligo dT and cDNA was synthesized from the mRNA. Synthetic adaptor oligonucleotides were ligated onto cDNA ends enabling its insertion into UNIZAP XR vector system (Stratagene), allowing high efficiency unidirectional (sense orientation) lambda library construction and the convenience of a plasmid system with blue/white color selection to detect clones with cDNA insertions. Alternative unidirectional vectors include but are not limited to pcDNAI (Invitrogen) and pSHlox-1 (Novagen). Double-stranded cDNA was blunted, ligated to EcoRI adaptors, digested with XhoI, size-selected, and cloned into the XhoI and EcoRI sites of the Lambda UNIZAP vector.

The cDNA library can be screened with either DNA probes or antibody probes and the pBLUESCRIPT phagemid (Stratagene) can be rapidly excised in vivo. The phagemid allows the use of a plasmid system for easy insert characterization, sequencing, site-directed mutagenesis, the creation of unidirectional deletions and expression of fusion proteins. The library phage particles were infected into XL1-BLUE E. coli host strain (Stratagene), which has a high transformation efficiency, increasing the probability of obtaining rare, under-represented clones in the cDNA library.

PROSTUT01 cDNA library

The PROSTUT01 cDNA library was constructed from prostate tumor tissue removed from a 50 year old Caucasian male. The tumor perforated and involved periprostatic tissue. There was also perineural invasion. The patient history revealed dysuria and treatment with an antibiotic. The patient had also reported a syncopal episode which did not require further treatment.

The frozen tissue was homogenized and lysed using a Brinkmann Polytron-PT 3000 homogenizer (Brinkmann Instruments, Inc. Westbury N.Y.) in guanidinium isothiocyanate solution. The lysate was extracted once with acid phenol at pH 4.0 per Stratagene's RNA isolation protocol (Stratagene Inc, San Diego Calif.). The lysate was re-extracted once more with phenol chloroform at pH 4.0. The RNA was then precipitated using 0.3 M sodium acetate and 2.5 volumes of ethanol, resuspended in DEPC-treated water and DNase treated for 25 min at 37° C. The RNA was again extracted three times with an equal volume of acid phenol, and reprecipitated using conditions described above. The mRNA was isolated using the OLIGOTEX kit (QIAGEN Inc, Chatsworth Calif.) and used to construct the cDNA library.

First strand cDNA synthesis was accomplished using an oligo d(T) primer/linker which also contained an XhoI restriction site. Second strand synthesis was performed using a combination of DNA polymerase I, E. coli ligase and RNase H, followed by the addition of an EcoRI adaptor to the blunt ended cDNA. The EcoRI adapted, double-stranded cDNA was then digested with XhoI restriction enzyme and fractionated on Sephacryl S400 to obtain sequences which exceeded 400 bp in size. The size selected cDNAs were inserted into the LAMPDAZAP vector system (Stratagene, La Jolla Calif.); and the vector which contains the PBLUESCRIPT phagemid (Stratagene) was transformed into cells of E. coli, strain XL1-BLUEMRF (Stratagene).

The phagemid forms of individual cDNA clones were obtained by the in vivo excision process. Enzymes from both PBluescript and a cotransformed f1 helper phage nicked the DNA, initiated new DNA synthesis, and created the smaller, single-stranded circular phagemid DNA molecules which contained the cDNA insert. The phagemid DNA was released, purified, and used to reinfect fresh host cells (SOLR, Stratagene). Presence of the phagemid which carries the gene for β-lactamase allowed transformed bacteria to grow on medium containing ampicillin.

II Isolation and sequencing of cDNA Clones

The phagemid forms of individual cDNA clones were obtained by the in vivo excision process, in which the host bacterial strain was coinfected with both the lambda library phage and an f1 helper phage. Proteins derived from both the library-containing phage and the helper phage nicked the lambda DNA, initiated new DNA synthesis from defined sequences on the lambda target DNA and created a smaller, single stranded circular phagemid DNA molecule that included all DNA sequences of the PBLUESCRIPT plasmid and the cDNA insert. The phagemid DNA was secreted from the cells and purified, then used to re-infect fresh host cells, where the double stranded phagemid DNA was produced. Because the phagemid carries the gene for β-lactamase, the newly-transformed bacteria are selected on medium containing ampicillin.

Phagemid DNA was purified using the QIAWELL-8 plasmid purification system or the QIAWELL PLUS or QIAWELL ULTRA DNA purification systems (QIAGEN Inc, Chatsworth Calif.). The DNA was eluted from the purification resin already prepared for DNA sequencing and other analytical manipulations.

The cDNA inserts from random isolates of the library were sequenced in part by the method of Sanger F and AR Coulson (1975; J Mol Biol 94:441f), using a Hamilton MICROLAB 2200 (Hamilton, Reno Nev.) in combination with four Peltier thermal cyclers (PTC200 from MJ Research, Watertown Mass.) and Applied Biosystems 377 or 373 DNA sequencing systems (Perkin Elmer), and the reading frame was determined.

III Homology Searching of cDNA Clones and Their Deduced Proteins

Each cDNA was compared to sequences in GenBank using a search algorithm developed by Applied Biosystems and incorporated into the INHERIT 670 sequence analysis system. In this algorithm, Pattern Specification Language (TRW Inc, Los Angeles Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT-670 sequence analysis system in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul S F (1993) J Mol Evol 36:290–300; Altschul, S F et al (1990) J Mol Biol 215:403–10), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV Northern Analysis

Northern analysis is a laboratory technique used to detect the presence of a transcript of a gene and involves the hybridization of a labelled nucleotide sequence to a membrane on which RNAs from a particular cell type or tissue have been bound (Sambrook et al. supra).

Analogous computer techniques using BLAST (Altschul S F 1993 and 1990, supra) are used to search for identical or related molecules in nucleotide databases such as GenBank or the LIFESEQ® database (Incyte Pharmaceuticals, Inc. Palo Alto Calif.). This analysis is much faster than multiple, membrane-based hybridizations. In addition, the sensitivity of the computer search can be modified to determine whether any particular match is categorized as exact or homologous.

The basis of the search is the product score which is defined as:

% sequence identity×% maximum BLAST score/100 and it takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of the search are reported as a list of 1) libraries in which the full length sequence, or parts thereof, is represented 2) the abundance of the sequence, and 3) the percent abundance. Abundance directly reflects the number of times a particular transcript is present in a cDNA library, and percent abundance is abundance divided by the total number of sequences examined in the library.

V Extension of TUPRO-Encoding Polynucleotides to Full Length or to Recover Regulatory Elements Full length TUPRO-encoding nucleic acid sequences (SEQ ID NO:2 or SEQ ID NO:4) are used to design oligonucleotide primers for extending a partial nucleotide sequence to full length or for obtaining 5' sequences from genomic libraries. One primer is synthesized to initiate extension in the antisense direction (XLR) and the other is synthesized to extend sequence in the sense direction (XLF). Primers allow the extension of the known TUPRO-encoding sequence "outward" generating amplicons containing new, unknown nucleotide sequence for the region of interest. The initial primers are designed from the cDNA using OLIGO 4.06 primer analysis software (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier thermal cycler (PTC200; MJ Research, Watertown Mass.) and the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 μl aliquot of the reaction mixture is analyzed by electrophoresis on a low concentration (about 0.6–0.8%) agarose mini-gel to determine which reactions were successful in extending the sequence. Bands thought to contain the largest products were selected and cut out of the gel. Further purification involves using a commercial gel extraction method such as QIAQUICK (QIAGEN Inc). After recovery of the DNA, Klenow enzyme was used to trim single-stranded, nucleotide overhangs creating blunt ends which facilitate religation and cloning.

After ethanol precipitation, the products are redissolved in 13 μl of ligation buffer, 1 μl T4-DNA ligase (15 units) and 1 μl T4 polynucleotide kinase are added, and the mixture is incubated at room temperature for 2–3 hours or overnight at 16° C. Competent E. coli cells (in 40 μl of appropriate media) are transformed with 3 μl of ligation mixture and cultured in 80 μl of SOC medium (Sambrook J et al, supra). After incubation for one hour at 37° C., the whole transformation mixture is plated on Luria Bertani (LB)-agar (Sambrook J et al, supra) containing 2×Carb. The following day, several colonies are randomly picked from each plate and cultured in 150 μl of liquid LB/2×Carb medium placed in an individual well of an appropriate, commercially-available, sterile 96-well microtiter plate. The following day, 5 μl of each overnight culture is transferred into a non-sterile 96-well plate and after dilution 1:10 with water, 5 μl of each sample is transferred into a PCR array.

For PCR amplification, 18 μl of concentrated PCR reaction mix (3.3×) containing 4 units of rTth DNA polymerase, a vector primer and one or both of the gene specific primers used for the extension reaction are added to each well. Amplification is performed using the following conditions:

| Step 1 | 94° C. for 60 sec |
| --- | --- |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions are run on agarose gels together with molecular weight markers. The sizes of the PCR products are compared to the original partial cDNAs, and appropriate clones are selected, ligated into plasmid and sequenced.

VI Labeling and Use of Hybridization Probes

Hybridization probes derived from SEQ ID NO:2 or SEQ ID NO:4 are employed to screen cDNAs, genomic DNAs or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 mCi of [$\gamma$-$^{32}$P] adenosine triphosphate (Amersham, Chicago Ill.) and T4 polynucleotide kinase (DuPont NEN®, Boston Mass.). The labeled oligonucleotides are substantially purified with Sephadex G-25 super fine resin column (Pharmacia). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR film (Kodak, Rochester N.Y.) is exposed to the blots, or the blots are exposed in a Phosphoimager cassette (Molecular Dynamics, Sunnyvale Calif.), hybridization patterns are compared visually.

VII Antisense Molecules

The TUPRO-encoding sequence, or any part thereof, is used to inhibit in vivo or in vitro expression of naturally occurring TUPRO. Although use of antisense oligonucleotides, comprising about 20 base-pairs, is specifically described, essentially the same procedure is used with larger cDNA fragments. An oligonucleotide based on the coding sequence of TUPRO, as shown in FIGS. 1A, 1B, 1C, 2A, 2B, and 2C, is used to inhibit expression of naturally occurring TUPRO. The complementary oligonucleotide is designed from the most unique 5' sequence as shown in FIGS. 1A, 1B, 1C, 2A, 2B, and 2C, and used either to inhibit transcription by preventing promoter binding to the upstream nontranslated sequence or translation of a TUPRO-encoding transcript by preventing the ribosome from binding. Using an appropriate portion of the leader and 5' sequence of SEQ ID NO:2 or SEQ ID NO:4, an effective antisense oligonucleotide includes any 15–20 nucleotides spanning the region which translates into the signal or early coding sequence of the polypeptide as shown in FIGS. 1A, 1B, 1C, 2A 2B, and 2C.

VIII Expression of TUPRO

Expression of the TUPRO is accomplished by subcloning the cDNAs into appropriate vectors and transfecting the vectors into host cells. In this case, the cloning vector, pSport, previously used for the generation of the cDNA library is used to express TUPRO in E. coli. Upstream of the cloning site, this vector contains a promoter for β-galactosidase, followed by sequence containing the amino-terminal Met and the subsequent 7 residues of β-galactosidase. Immediately following these eight residues is a bacteriophage promoter useful for transcription and a linker containing a number of unique restriction sites.

Induction of an isolated, transfected bacterial strain with IPTG using standard methods produces a fusion protein which consists of the first seven residues of β-galactosidase, about 5 to 15 residues of linker, and the full length TUPRO-encoding sequence. The signal sequence directs the secretion of TUPRO into the bacterial growth media which can be used directly in the following assay for activity.

IX TUPRO Activity

TUPRO's ability to form either homodimers or heterodimers with human D52 can be measured by a common immunoprecipitation technique, such as described by Heymach J V et al (1995, J Biol Chem 270: 12297–12304). Human D52 and D53 rabbit antisera is raised against peptides corresponding to internal sequences in which the two proteins share no amino acid identity. COS cells are transiently transfected with vector alone or expression plasmids for human D52, TUPRO, or both, and conditioned media from the transfectants is analyzed directly or after immunoprecipitation with anti-D52 or anti-TUPRO monoclonal antibody. Samples are run by SDS-PAGE and immunoblotted. Duplicate immunoblots are probed with either D52 or TUPRO antisera (Heymach et al, supra). Secondary antibodies conjugated to peroxidase are used to reveal homodimers and heterodimer formation.

X Production of TUPRO Specific Antibodies

TUPRO substantially purified using PAGE electrophoresis (Sambrook, supra) is used to immunize rabbits and to produce antibodies using standard protocols. The amino acid sequence translated from TUPRO is analyzed using DNASTAR software (DNAStar Inc) to determine regions of high immunogenicity and a corresponding oligopolypeptide is synthesized and used to raise antibodies by means known to those of skill in the art. Analysis to select appropriate epitopes, such as those near the C-terminus or in hydrophilic regions (shown in FIGS. 7 and 9) is described by Ausubel F M et al (supra).

Typically, the oligopeptides are 15 residues in length, synthesized using an Applied Biosystems 431A peptide synthesizer using fmoc-chemistry, and coupled to keyhole limpet hemocyanin (KLH, Sigma) by reaction with M-maleimidobenzoyl-N-hydroxysuccinimide ester (MBS; Ausubel F M et al, supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring TUPRO Using Specific Antibodies

Naturally occurring or recombinant TUPRO is substantially purified by immunoaffinity chromatography using antibodies specific for TUPRO. An immunoaffinity column is constructed by covalently coupling TUPRO antibody to an activated chromatographic resin such as CnBr-activated SEPHAROSE (Pharmacia Biotech). After the coupling, the resin is blocked and washed according to the manufacturer's instructions.

Media containing TUPRO is passed over the immunoaffinity column, and the column is washed under conditions that allow the preferential absorbance of TUPRO (eg, high ionic strength buffers in the presence of detergent). The column is eluted under conditions that disrupt antibody/TUPRO binding (eg, a buffer of pH 2–3 or a high concentration of a chaotrope such as urea or thiocyanate ion), and TUPRO is collected.

XII Identification of Molecules Which Interact with TUPRO

TUPRO, or biologically active fragments thereof, are labelled with $^{125}$I Bolton-Hunter reagent (Bolton, A E and Hunter, W M (1973) Biochem J 133: 529). Candidate molecules previously arrayed in the wells of a 96 well plate are incubated with the labelled TUPRO, washed and any wells with labelled TUPRO complex are assayed. Data obtained using different concentrations of TUPRO are used to calculate values for the number, affinity, and association of TUPRO with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

We claim:

1. A substantially purified polypeptide comprising the amino acid sequence of SEQ ID NO:3.

2. A composition comprising a substantially purified polypeptide as in claim 1 in conjunction with a suitable pharmaceutical carrier.

3. A purified antibody which binds specifically to the polypeptide of claim 1.

4. A method of screening for a compound which specifically binds to the polypeptide of claim 1, said method comprising the steps of:

a) providing a plurality of compounds;

b) contacting the polypeptide of claim 1 with said plurality of compounds; and c) detecting binding of the polypeptide to at least one of said plurality of compounds, thereby identifying the compound which specifically binds to the polypeptide of claim 1.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
        (A) LENGTH: 204 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY:
        (B) CLONE: Consensus (xi) SEQUENCE DESCRIPTION: SEQ ID NO:1:

```
Met Glu Ala Gln Ala Gln Gly Leu Leu Glu Thr Glu Pro Leu Gln Gly
 1               5                  10                  15

Thr Asp Glu Asp Ala Val Ala Ser Ala Asp Phe Ser Ser Met Leu Ser
                20                  25                  30

Glu Glu Glu Lys Glu Glu Leu Lys Ala Glu Leu Val Gln Leu Glu Asp
            35                  40                  45

Glu Ile Thr Thr Leu Arg Gln Val Leu Ser Ala Lys Glu Arg His Leu
    50                  55                  60

Val Glu Ile Lys Gln Lys Leu Gly Met Asn Leu Met Asn Glu Leu Lys
65                  70                  75                  80

Gln Asn Phe Ser Lys Ser Trp His Asp Met Gln Thr Thr Thr Ala Tyr
                85                  90                  95

Lys Lys Thr His Glu Thr Leu Ser His Ala Gly Gln Lys Ala Thr Ala
            100                 105                 110

Ala Phe Ser Asn Val Gly Thr Ala Ile Ser Lys Lys Phe Gly Asp Met
            115                 120                 125

Ser Tyr Ser Ile Arg His Ser Ile Ser Met Pro Ala Met Arg Asn Ser
    130                 135                 140

Pro Thr Phe Lys Ser Phe Glu Glu Arg Val Glu Thr Thr Val Thr Ser
145                 150                 155                 160

Leu Lys Thr Lys Val Gly Gly Thr Asn Pro Asn Gly Gly Ser Phe Glu
                165                 170                 175

Glu Val Leu Ser Ser Thr Ala His Ala Ser Ala Gln Ser Leu Ala Gly
```

```
                 180                 185                 190
Gly Ser Arg Arg Thr Lys Glu Glu Glu Leu Gln Cys
        195                 200

(2) INFORMATION FOR SEQ ID NO:2:

(i) SEQUENCE CHARACTERISTICS:
        (A) LENGTH: 790 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY:
        (B) CLONE: Consensus (xi) SEQUENCE DESCRIPTION: SEQ ID NO:2:

GGGCCAGCTG CGTTCTGAGC CTGGGCGCAG CTACCATCTG CTCTGGGAAG CACCAGGGTG      60

TCCCCGCCGC CCTCAGCTCG AAGTCAGCCA CCATGGAGGC GCAGGCACAA GGTTTGTTGG     120

AGACTGAACC GTTGCAAGGA ACAGACGAAG ATGCAGTAGC CAGTGCTGAC TTCTCTAGCA     180

TGCTCTCTGA GGAGGAAAAG GAAGAGTTAA AAGCAGAGTT AGTTCAGCTA GAAGACGAAA     240

TTACAACACT ACGACAAGTT TTGTCAGCGA AGAAAGGCA TCTAGTTGAG ATAAAACAAA     300

AACTCGGCAT GAACCTGATG AATGAATTAA AACAGAACTT CAGCAAAAGC TGGCATGACA     360

TGCAGACTAC CACTGCCTAC AAGAAAACAC ATGAAACCCT GAGTCACGCA GGGCAAAAGG     420

CAACTGCAGC TTTCAGCAAC GTTGGAACGG CCATCAGCAA GAAGTTCGGA GACATGAGTT     480

ACTCCATTCG CCATTCCATA AGTATGCCTG CTATGAGGAA TTCTCCTACT TTCAAATCAT     540

TTGAGGAGAG GGTTGAGACA ACTGTCACAA GCCTCAAGAC GAAAGTAGGC GGTACGAACC     600

CTAATGGAGG CAGTTTTGAG GAGGTCCTCA GCTCCACGGC CCATGCCAGT GCCCAGAGCT     660

TGGCAGGAGG CTCCCGGCGG ACCAAGGAGG AGGAGCTGCA GTGCTAAGTC CAGCCAGCGT     720

GCAGTGCATC CAGAAACCGG CCACTACCCA GCCCATCTNT GCCTGTGCTT ATCCAGATAA     780

GAAGACCAAA                                                          790

(2) INFORMATION FOR SEQ ID NO:3:

(i) SEQUENCE CHARACTERISTICS:
        (A) LENGTH: 245 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY:
        (B) CLONE: Consensus (xi) SEQUENCE DESCRIPTION: SEQ ID NO:3:

Met Thr Leu Phe His Phe Gly Asn Cys Phe Ala Leu Ala Tyr Phe Pro
1               5                  10                  15

Tyr Phe Ile Thr Tyr Lys Cys Ser Gly Leu Ser Glu Tyr Asn Ala Phe
            20                  25                  30

Trp Lys Cys Val Gln Ala Gly Val Thr Tyr Leu Phe Val Gln Leu Cys
        35                  40                  45

Lys Met Leu Phe Leu Ala Thr Phe Phe Pro Thr Trp Glu Gly Gly Ile
    50                  55                  60
```

-continued

```
Tyr Asp Phe Ile Gly Glu Phe Met Lys Ala Ser Val Asp Val Ala Asp
 65                  70                  75                  80

Leu Ile Gly Leu Asn Leu Val Met Ser Arg Asn Ala Gly Lys Gly Glu
                 85                  90                  95

Tyr Lys Ile Met Val Ala Ala Leu Gly Trp Ala Thr Ala Glu Leu Ile
                100                 105                 110

Met Ser Arg Cys Ile Pro Leu Trp Val Gly Ala Arg Gly Ile Glu Phe
            115                 120                 125

Asp Trp Lys Tyr Ile Gln Met Ser Ile Asp Ser Asn Ile Ser Leu Val
130                 135                 140

His Tyr Ile Val Ala Ser Ala Gln Val Trp Met Ile Thr Arg Tyr Asp
145                 150                 155                 160

Leu Tyr His Asn Phe Arg Pro Ala Val Leu Leu Met Phe Leu Ser
                165                 170                 175

Val Tyr Lys Ala Phe Val Met Glu Thr Phe Val His Leu Cys Ser Leu
            180                 185                 190

Gly Ser Trp Ala Arg Leu Asp Ala Arg Ala Val Val Thr Gly Leu Leu
            195                 200                 205

Ala Leu Lys His Phe Gly Pro Val Cys Arg Arg Cys Gln Cys Ala Leu
            210                 215                 220

Leu Gly Leu Val Ser Gln Thr Leu Met Tyr Leu Phe Pro Ala Ser Leu
225                 230                 235                 240

Gln Val Leu Val Lys
                245
```

(2) INFORMATION FOR SEQ ID NO:4:

(i) SEQUENCE CHARACTERISTICS:
       (A) LENGTH: 888 base pairs
       (B) TYPE: nucleic acid
       (C) STRANDEDNESS: single
       (D) TOPOLOGY: linear (ii) MOLECULE TYPE: cDNA (vii) IMMEDIATE SOURCE:
       (A) LIBRARY:
       (B) CLONE: Consensus (xi) SEQUENCE DESCRIPTION: SEQ ID NO:4:

```
GTMGMKCGCG GGCCCCCGCC AGTCAGGTGG GTGCCAGGCC CTGGCCGTGG CGAAAGAGCC    60

GGCGGAGGGA GGACCCGCTC CCGGAGACGC CGCCTCGCGA TCCCCGCGCG GGCGGGACCG   120

GGCGGCCGGC ATCATGACCC TGTTTCACTT CGGGAACTGC TTCGCTCTTG CCTACTTCCC   180

CTACTTCATC ACCTACAAGT GCAGCGGCCT GTCCGAGTAC AACGCCTTCT GGAAATGCGT   240

CCAGGCTGGA GTCACCTACC TCTTTGTCCA ACTCTGCAAG ATGCTGTTCT TGGCCACTTT   300

CTTTCCCACC TGGGAAGGCG GCATCTATGA CTTCATTGGG GAGTTCATGA AGGCCAGCGT   360

GGATGTGGCA GACCTGATAG GTCTAAACCT TGTCATGTCC CGGAATGCCG GCAAGGGAGA   420

GTACAAGATC ATGGTTGCTG CCCTGGGCTG GGCCACTGCT GAGCTTATTA TGTCCCGCTG   480

CATTCCCCTA TGGGTCGGAG CCCGGGGCAT TGAGTTTGAC TGGAAGTACA TCCAGATGAG   540

CATAGACTCC AACATCAGTC TGGTCCATTA CATCGTCGCG TCTGCTCAGG TCTGGATGAT   600

AACACGCTAT GATCTGTACC ACAACTTCCG GCCAGCTGTC CTTCTGCTGA TGTTCCTCAG   660

TGTCTACAAG GCCTTTGTTA TGGAGACCTT CGTCCACCTC TGCTCGCTGG GCAGTTGGGC   720

ARCTCTAMTG GCCCGAGCAG TGGTAACGGG GCTGCTGGCC CTCAAGCACT TTGGSCCTGT   780
```

```
ATGTCGSCGT TGTCAATGTG CACTYCTAGG CTTGGTGTCT CAGACATTGA TGTACCTTTT    840

CCCTGCCTCA CTCCAGGTTT TAGTGAAGTA AACAGTATTT GGAAAGTT              888
```

(2) INFORMATION FOR SEQ ID NO:5:

(i) SEQUENCE CHARACTERISTICS:
        (A) LENGTH: 184 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: 790225

(xi) SEQUENCE DESCRIPTION: SEQ ID NO:5:

```
Met Asp Arg Gly Glu Gln Gly Leu Leu Arg Thr Asp Pro Val Pro Glu
 1               5                  10                  15

Glu Gly Glu Asp Val Ala Ala Thr Ile Ser Ala Thr Glu Thr Leu Ser
            20                  25                  30

Glu Glu Glu Gln Glu Glu Leu Arg Arg Glu Leu Ala Lys Val Glu Glu
        35                  40                  45

Glu Ile Gln Thr Leu Ser Gln Val Leu Ala Ala Lys Glu Lys His Leu
50                  55                  60

Ala Glu Ile Lys Arg Lys Leu Gly Ile Asn Ser Leu Gln Glu Leu Lys
65                  70                  75                  80

Gln Asn Ile Ala Lys Gly Trp Gln Asp Val Thr Ala Thr Ser Ala Tyr
                85                  90                  95

Lys Lys Thr Ser Glu Thr Leu Ser Gln Ala Gly Gln Lys Ala Ser Ala
            100                 105                 110

Ala Phe Ser Ser Val Gly Ser Val Ile Thr Lys Lys Leu Glu Asp Val
        115                 120                 125

Lys Asn Ser Pro Thr Phe Lys Ser Phe Glu Glu Lys Val Glu Asn Leu
    130                 135                 140

Lys Ser Lys Val Gly Gly Thr Lys Pro Ala Gly Gly Asp Phe Gly Glu
145                 150                 155                 160

Val Leu Asn Ser Ala Ala Asn Ala Ser Ala Thr Thr Thr Glu Pro Leu
                165                 170                 175

Pro Glu Lys Thr Gln Glu Ser Leu
            180
```

(2) INFORMATION FOR SEQ ID NO:6:

(i) SEQUENCE CHARACTERISTICS:
        (A) LENGTH: 257 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: 1072344

(xi) SEQUENCE DESCRIPTION: SEQ ID NO:6:

```
Met Pro Lys Gly Asn Lys Lys Pro Asn Glu Lys Lys Glu Glu Leu Glu
 1               5                  10                  15

Lys Phe Ala Lys Glu Leu Gln Gly Ser Asp Ser Asp Glu Asp Ala Val
            20                  25                  30
```

-continued

```
Val Ile Glu Gln Pro Thr Val Glu Pro Lys Leu Pro Gln Asn Asp Ser
            35                  40                  45

Ser Ser Ser Asn Lys Ile Val Leu Ser Gln Ala Glu Lys Asp Leu Leu
 50                  55                  60

Arg Thr Glu Leu Asp Lys Thr Glu Glu Ile Ser Thr Leu Lys Gln
 65                  70                  75                  80

Val Leu Ser Ala Arg Gln Lys His Ala Ala Glu Leu Lys Arg Lys Leu
                 85                  90                  95

Gly Leu Thr Pro Phe Ser Glu Leu Ser Gln Asp Ile Asn Arg Ser Leu
                100                 105                 110

Lys Thr Val Thr Asp Thr Asp Ala Cys Thr His Phe Ile Glu Ile Asn
            115                 120                 125

Ile Gln Lys Lys Lys Lys Gln Ser Met Tyr Tyr Ile Lys Arg Leu Ser
        130                 135                 140

Lys Asn Ile Gln Thr Val Pro Ile Leu Thr Ser Glu Lys Lys Arg Ile
145                 150                 155                 160

Leu His Ala Phe Ile Val Leu Lys Lys Ser Ser Ile Leu Lys Ser
                165                 170                 175

Leu Leu Leu Trp Gln Gln Tyr Gln Lys Thr Ala Glu Val Ala Ala Ala
                180                 185                 190

Thr Ser Asp Thr Val Lys Glu Lys Trp Asn Asp Met Arg Asn Ser Ser
            195                 200                 205

Leu Phe Lys Ser Phe Glu Ser Lys Leu Gly Ser Ala Leu Asn Asn Ala
        210                 215                 220

Lys Met Ala Ala Ser Thr Ser Ile Asp His Leu Ala Gly Ala Ala Arg
225                 230                 235                 240

Gly Pro Ser Gln Thr Gly Thr Pro Val Ala Glu Glu Ala Lys Pro Ile
                245                 250                 255

Ser
```

(2) INFORMATION FOR SEQ ID NO:7:

(i) SEQUENCE CHARACTERISTICS:
        (A) LENGTH: 216 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: 470373

(xi) SEQUENCE DESCRIPTION: SEQ ID NO:7:

```
Met Ser Phe Phe His Phe Ile Asn Cys Phe Ala Leu Ala Phe Ala Pro
 1               5                  10                  15

Tyr Phe Ile Val Tyr Lys Tyr Ser Gly Ile Asn Glu Tyr Ser Ser Ile
            20                  25                  30

Trp Lys Cys Ala Thr Ala Ser Gly Gly Tyr Leu Leu Thr Gln Leu Ala
        35                  40                  45

Lys Leu Leu Ile Ile Ala Thr Phe Phe Pro Ala Leu Asp Ser Glu Gly
    50                  55                  60

Phe Ser Ile Val Pro Glu Phe Leu Lys Ser Ser Ala Asp Ile Ile Asp
65                  70                  75                  80

Val Ile Gly Leu His Leu Leu Met Thr Asn Phe Leu Ala Gly Lys Gly
                85                  90                  95
```

-continued

```
Glu Val Arg Phe Val Val Gly Gly Leu Gly Trp Gly Phe Ala His Ser
            100                 105                 110

Val Ala His Arg Leu Val Leu Leu Trp Val Gly Ala Arg Gly Thr Ala
            115                 120                 125

Phe Thr Trp Arg Trp Val Gln Thr Ser Leu Asp Ser Ser Ala Asp Leu
            130                 135                 140

Leu Val Ile Val Ser Leu Ala Cys Leu Thr Trp Met Ile Thr Arg Thr
145                 150                 155                 160

Pro Asn Lys Phe Leu Val Ser Pro Ile Leu Ala Ile Thr Val Gln His
                165                 170                 175

Thr Phe Ser Leu Tyr Gly Trp Ser Leu Leu Ala Phe Arg Phe Ala Tyr
                180                 185                 190

Ser Ile Ala Thr Ala Ile Leu Thr Val Val Val Tyr Ser Ala Asn Arg
                195                 200                 205

Thr Ala Ser Thr Arg Lys Asn Glu
210                 215
```